United States Patent
Bacich et al.

(10) Patent No.: US 11,311,313 B2
(45) Date of Patent: *Apr. 26, 2022

(54) APPARATUS AND METHODS FOR ACCESSING AND SEALING BODILY VESSELS AND CAVITIES

(71) Applicant: CrossBay Medical, Inc., San Diego, CA (US)

(72) Inventors: Steven R. Bacich, Half Moon Bay, CA (US); Matthew Thomas Yurek, San Diego, CA (US); Piush Vidyarthi, San Rafael, CA (US)

(73) Assignee: CrossBay Medical, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/749,659

(22) Filed: Jan. 22, 2020

(65) Prior Publication Data
US 2020/0163699 A1 May 28, 2020

Related U.S. Application Data

(60) Continuation of application No. 16/236,149, filed on Dec. 28, 2018, now Pat. No. 10,820,927, which is a
(Continued)

(51) Int. Cl.
*A61B 17/43* (2006.01)
*A61M 39/24* (2006.01)
(Continued)

(52) U.S. Cl.
CPC .......... *A61B 17/43* (2013.01); *A61B 1/00082* (2013.01); *A61B 1/303* (2013.01);
(Continued)

(58) Field of Classification Search
CPC ................ A61B 17/43; A61B 17/1204; A61B 17/12136; A61B 17/0218; A61B 17/3423;
(Continued)

(56) References Cited

U.S. PATENT DOCUMENTS 3,452,749 A 7/1969 Riedell
3,500,819 A 3/1970 Silverman
(Continued)

FOREIGN PATENT DOCUMENTS

CN 103566683 2/2014
EP 0359489 3/1990
(Continued)

OTHER PUBLICATIONS

U.S. Appl. No. 14/495,726, filed Sep. 24, 2014.
(Continued)

*Primary Examiner* — Anh T Dang
(74) *Attorney, Agent, or Firm* — Levine Bagade Han LLP

(57) ABSTRACT

Everting balloon systems and methods for using the same are disclosed herein. The systems can be configured to access and dilate body lumen and cavities. For example, the systems can be used to dilate the cervix and access the uterine cavity. The systems can also be used to occlude the cervix. The systems can also be used to occlude the urethra.

19 Claims, 22 Drawing Sheets

Related U.S. Application Data continuation of application No. 15/960,209, filed on Apr. 23, 2018, now Pat. No. 10,582,951, which is a division of application No. 15/690,096, filed on Aug. 29, 2017, now Pat. No. 9,949,756, which is a continuation of application No. 14/525,043, filed on Oct. 27, 2014, now Pat. No. 10,245,074.

(60) Provisional application No. 62/007,339, filed on Jun. 3, 2014, provisional application No. 62/005,355, filed on May 30, 2014, provisional application No. 61/977,478, filed on Apr. 9, 2014, provisional application No. 61/902,742, filed on Nov. 11, 2013.

(51) Int. Cl.

| | | |
|---|---|---|
| *A61M 25/10* | (2013.01) | |
| *A61B 1/00* | (2006.01) | |
| *A61B 1/303* | (2006.01) | |
| *A61B 1/32* | (2006.01) | |
| *A61B 17/02* | (2006.01) | |
| *A61B 17/34* | (2006.01) | |
| *A61M 29/02* | (2006.01) | |
| *A61B 17/12* | (2006.01) | |
| *A61F 6/18* | (2006.01) | |
| *A61F 6/22* | (2006.01) | |
| *A61M 25/01* | (2006.01) | |
| *A61F 2/00* | (2006.01) | |
| *A61B 17/00* | (2006.01) | |
| *A61B 17/42* | (2006.01) | |
| *A61D 19/02* | (2006.01) | |
| *A61D 19/04* | (2006.01) | |
| *A61B 17/29* | (2006.01) | |
| *A61M 25/00* | (2006.01) | |
| *A61B 90/00* | (2016.01) | |

(52) U.S. Cl.
CPC ............ *A61B 1/32* (2013.01); *A61B 17/0218* (2013.01); *A61B 17/1204* (2013.01); *A61B 17/12099* (2013.01); *A61B 17/12136* (2013.01); *A61B 17/3423* (2013.01); *A61F 2/0027* (2013.01); *A61F 6/18* (2013.01); *A61F 6/22* (2013.01); *A61M 25/0119* (2013.01); *A61M 25/10* (2013.01); *A61M 25/1002* (2013.01); *A61M 25/1011* (2013.01); *A61M 25/1025* (2013.01); *A61M 25/10181* (2013.11); *A61M 25/10182* (2013.11); *A61M 29/02* (2013.01); *A61M 39/24* (2013.01); *A61B 2017/00115* (2013.01); *A61B 2017/00557* (2013.01); *A61B 2017/00805* (2013.01); *A61B 2017/0225* (2013.01); *A61B 2017/2946* (2013.01); *A61B 2017/345* (2013.01); *A61B 2017/3435* (2013.01); *A61B 2017/4216* (2013.01); *A61B 2017/4225* (2013.01); *A61B 2090/037* (2016.02); *A61B 2090/0807* (2016.02); *A61B 2090/0809* (2016.02); *A61B 2090/0811* (2016.02); *A61D 19/027* (2013.01); *A61D 19/04* (2013.01); *A61M 25/104* (2013.01); *A61M 2025/0004* (2013.01); *A61M 2025/0175* (2013.01); *A61M 2025/1004* (2013.01); *A61M 2025/1013* (2013.01); *A61M 2025/1052* (2013.01); *A61M 2025/1059* (2013.01); *A61M 2025/1065* (2013.01)

(58) Field of Classification Search
CPC ...... A61B 17/12099; A61B 2017/3435; A61B 1/0082; A61B 1/303; A61B 1/32; A61M 25/10; A61M 25/0119; A61M 25/1011; A61M 25/1025; A61M 25/10181; A61M 25/10182; A61M 39/24; A61M 29/02; A61M 2025/1052; A61F 6/18; A61F 6/22; A61F 2/0027

See application file for complete search history.

(56) References Cited

U.S. PATENT DOCUMENTS

| | | |
|---|---|---|
| 3,825,013 A | 7/1974 | Craven |
| 3,882,852 A | 5/1975 | Sinnreich |
| 3,911,927 A | 10/1975 | Rich et al. |
| 3,982,544 A | 9/1976 | Dyck |
| 4,271,839 A | 6/1981 | Fogarty et al. |
| 4,654,027 A | 3/1987 | Dragan et al. |
| 4,857,054 A | 8/1989 | Helfer |
| 4,946,440 A | 8/1990 | Hall |
| 5,152,277 A | 10/1992 | Honda et al. |
| 5,211,627 A | 5/1993 | William |
| 5,284,473 A | 2/1994 | Calabria |
| 5,364,345 A | 11/1994 | Lowery et al. |
| 5,374,247 A | 12/1994 | Lowery et al. |
| 5,376,084 A | 12/1994 | Bacich |
| 5,383,889 A | 1/1995 | Warner et al. |
| 5,389,089 A | 2/1995 | Bauer |
| 5,458,573 A | 10/1995 | Summers |
| 5,531,219 A | 7/1996 | Rosenberg |
| 5,630,797 A | 5/1997 | Diedrich et al. |
| 5,662,582 A | 9/1997 | Levius et al. |
| 5,724,994 A | 3/1998 | Simon et al. |
| 5,925,058 A | 7/1999 | Smith et al. |
| 5,954,688 A | 9/1999 | Adams et al. |
| 5,964,223 A | 10/1999 | Baran |
| 6,039,721 A | 3/2000 | Johnson et al. |
| 6,042,535 A | 3/2000 | Porter |
| 6,080,129 A | 6/2000 | Blaisdell |
| 6,090,083 A | 7/2000 | Sell |
| 6,119,695 A | 9/2000 | Augustine et al. |
| 6,398,775 B1 | 6/2002 | Perkins et al. |
| 6,436,118 B1 | 8/2002 | Kayan |
| 6,450,963 B1 | 9/2002 | Ackerman |
| 6,530,898 B1 | 3/2003 | Nimkar et al. |
| 6,729,334 B1 | 5/2004 | Baran |
| 7,220,252 B2 | 5/2007 | Shah |
| 7,556,060 B2 | 7/2009 | Guala |
| 7,727,155 B2 | 6/2010 | De Ziegler |
| 7,789,893 B2 | 9/2010 | Drasler et al. |
| 8,221,403 B2 | 7/2012 | Sharkey et al. |
| 8,551,001 B2 | 10/2013 | Connor et al. |
| 9,326,790 B2 | 5/2016 | Chin et al. |
| 9,949,756 B2 | 4/2018 | Bacich |
| 10,034,986 B2 | 7/2018 | Yurek et al. |
| 10,245,074 B2 | 4/2019 | Bacich et al. |
| 10,582,951 B2 | 3/2020 | Bacich |
| 10,646,256 B2 | 5/2020 | Bacich et al. |
| 10,820,927 B2 | 11/2020 | Bacich et al. |
| 11,141,308 B2 | 10/2021 | Bacich et al. |
| 2002/0108614 A1 | 8/2002 | Schultz |
| 2002/0111602 A1 | 8/2002 | Ackerman et al. |
| 2003/0023263 A1 | 1/2003 | Krolik et al. |
| 2003/0208223 A1 | 11/2003 | Kleiner |
| 2004/0231668 A1 | 11/2004 | Kates |
| 2005/0015047 A1 | 1/2005 | Shah |
| 2005/0154415 A1 | 7/2005 | Fogarty et al. |
| 2005/0277811 A1 | 12/2005 | Richards et al. |
| 2007/0203472 A1 | 8/2007 | Nachmani |
| 2008/0167629 A1 | 7/2008 | Dann et al. |
| 2008/0183038 A1 | 7/2008 | Tilson et al. |
| 2009/0048685 A1 | 2/2009 | Frigstad et al. |
| 2009/0126731 A1 | 5/2009 | Dunsmore et al. |
| 2009/0199848 A1 | 8/2009 | Sharratt |
| 2009/0293873 A1 | 12/2009 | Djupesland et al. |
| 2009/0299327 A1 | 12/2009 | Tilson et al. |
| 2010/0086492 A1 | 4/2010 | Lee-sepsick et al. |
| 2010/0147701 A1 | 6/2010 | Field |
| 2011/0060276 A1 | 3/2011 | Schaeffer et al. |
| 2011/0313400 A1 | 12/2011 | Boatman |

(56) References Cited

U.S. PATENT DOCUMENTS

| | | |
|---|---|---|
| 2012/0035471 A1 | 2/2012 | Lee-Sepsick et al. |
| 2012/0065674 A1 | 3/2012 | Levy |
| 2012/0230915 A1 | 9/2012 | Exalto et al. |
| 2013/0178785 A1 | 7/2013 | Papay et al. |
| 2013/0253426 A1 | 9/2013 | Campbell et al. |
| 2014/0114261 A1 | 4/2014 | Geppert et al. |
| 2014/0155745 A1 | 6/2014 | Duncan |
| 2014/0166011 A1 | 6/2014 | Pierro et al. |
| 2014/0283820 A1 | 9/2014 | Flickinger et al. |
| 2015/0040902 A1 | 2/2015 | Blum |
| 2015/0065951 A1 | 3/2015 | Freyman et al. |
| 2015/0133727 A1 | 5/2015 | Bacich et al. |
| 2015/0133779 A1 | 5/2015 | Yurek et al. |
| 2015/0142045 A1 | 5/2015 | Bacich et al. |
| 2015/0335354 A1 | 11/2015 | Carson et al. |
| 2016/0278747 A1 | 9/2016 | Chin et al. |
| 2016/0317288 A1 | 11/2016 | Rogers et al. |
| 2017/0354437 A1 | 12/2017 | Bacich |
| 2018/0235660 A1 | 8/2018 | Bacich |
| 2018/0333545 A1 | 11/2018 | Yurek et al. |
| 2018/0360424 A1 | 12/2018 | Yurek et al. |
| 2019/0009058 A1 | 1/2019 | Bacich et al. |
| 2019/0126010 A1 | 5/2019 | Sarna et al. |
| 2019/0167308 A1 | 6/2019 | Bacich et al. |
| 2019/0223913 A1 | 7/2019 | Bacich et al. |
| 2019/0366048 A9 | 12/2019 | Bacich et al. |
| 2020/0023162 A1 | 1/2020 | Bacich et al. |
| 2020/0206463 A1 | 7/2020 | Bacich et al. |
| 2020/0297384 A1 | 9/2020 | Bacich et al. |
| 2020/0330131 A1 | 10/2020 | Bacich et al. |
| 2020/0397478 A1 | 12/2020 | Bacich et al. |
| 2021/0106457 A1 | 4/2021 | Bacich et al. |
| 2021/0106458 A1 | 4/2021 | Bacich et al. |
| 2021/0196503 A1 | 7/2021 | Bacich et al. |
| 2021/0251800 A9 | 8/2021 | Bacich et al. |

FOREIGN PATENT DOCUMENTS

| | | |
|---|---|---|
| EP | 0692273 | 1/1996 |
| WO | WO 1993/007927 | 4/1993 |
| WO | WO 1994/025099 | 11/1994 |
| WO | WO 1997/021461 | 6/1997 |
| WO | WO 2009/042621 | 4/2009 |
| WO | WO 2010/055701 | 5/2010 |
| WO | WO 2015/069952 | 5/2015 |
| WO | WO 2017/151918 | 9/2017 |
| WO | WO 2019/010244 | 1/2019 |
| WO | WO 2019/046800 | 3/2019 |
| WO | WO 2021/072261 | 4/2021 |

OTHER PUBLICATIONS

U.S. Appl. No. 14/524,980, filed Oct. 27, 2014.
U.S. Appl. No. 14/525,012, filed Oct. 27, 2014.
U.S. Appl. No. 14/525,043, filed Oct. 27, 2014.
U.S. Appl. No. 15/690,096, filed Aug. 29, 2017.
U.S. Appl. No. 15/960,209, filed Apr. 23, 2018.
U.S. Appl. No. 16/029,305, filed Jul. 6, 2018.
U.S. Appl. No. 16/049,680, filed Jul. 30, 2018.
U.S. Appl. No. 16/110,447, filed Aug. 23, 2018.
U.S. Appl. No. 16/236,149, filed Dec. 28, 2018.
U.S. Appl. No. 16/370,340, filed Mar. 29, 2019.

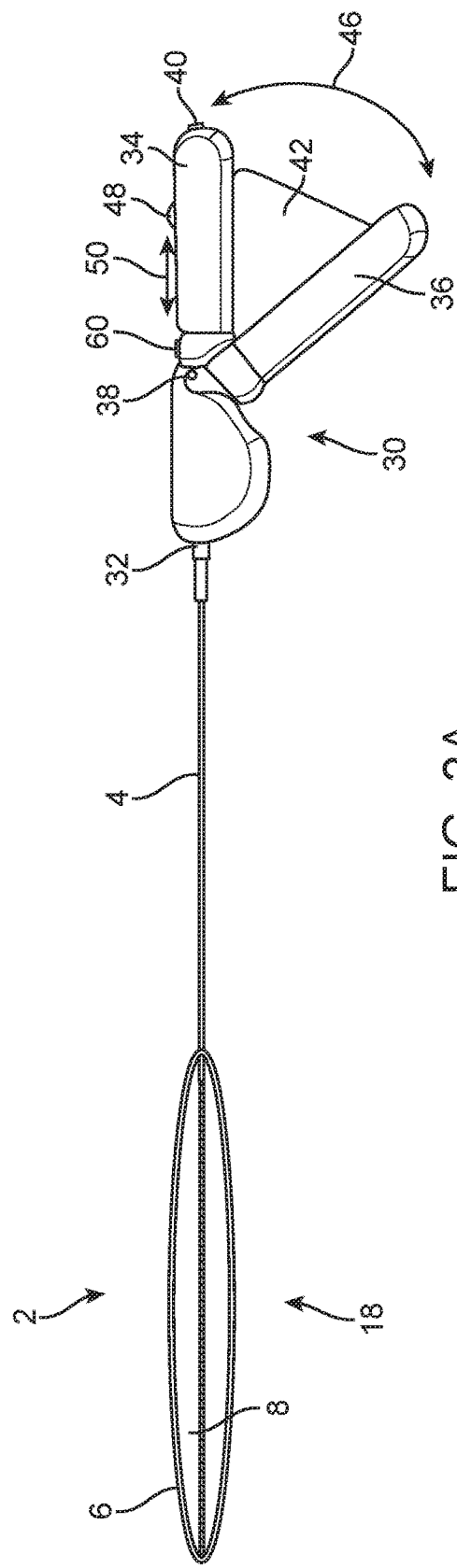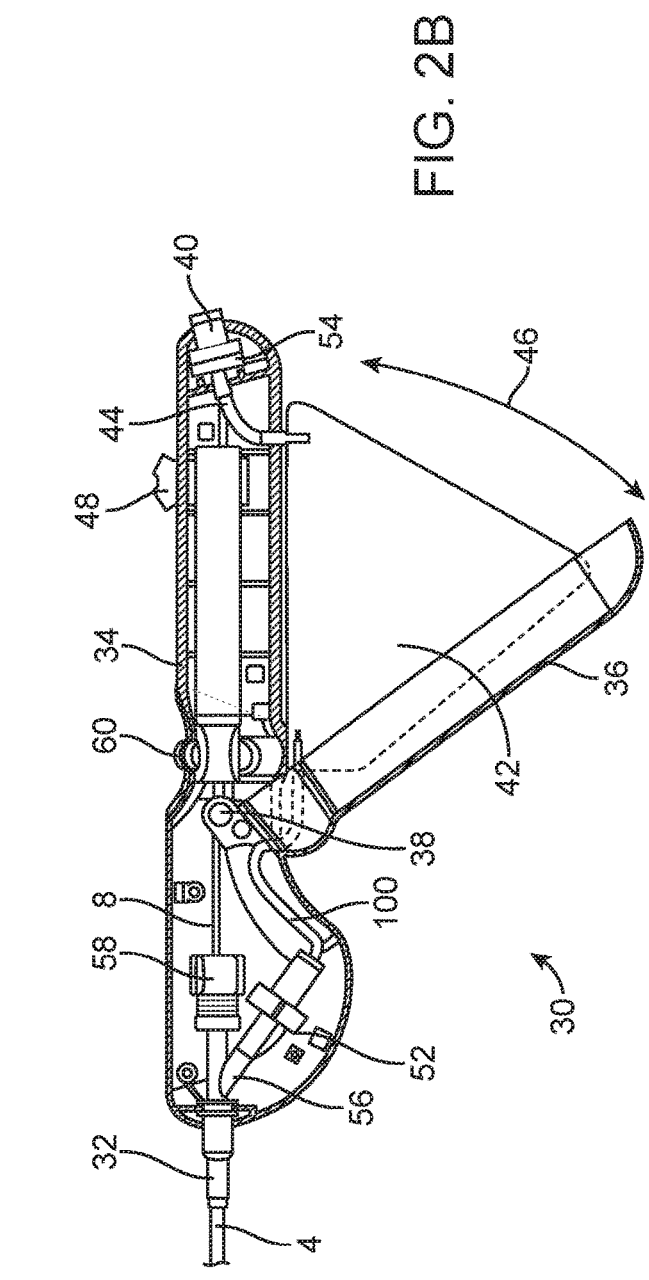
FIG. 2A
FIG. 2B

APPARATUS AND METHODS FOR ACCESSING AND SEALING BODILY VESSELS AND CAVITIES

CROSS-REFERENCE TO RELATED APPLICATIONS

This application is a continuation of U.S. patent application Ser. No. 16/236,149, filed Dec. 28, 2018, which is a continuation of U.S. patent application Ser. No. 15/960,209, filed Apr. 23, 2018, which is a divisional application of U.S. patent application Ser. No. 15/690,096, filed Aug. 29, 2017, issued as U.S. Pat. No. 9,949,756, which is a continuation of U.S. patent application Ser. No. 14/525,043, filed Oct. 27, 2014, issued as U.S. Pat. No. 10,245,074, which claims priority to U.S. Provisional Application Nos. 61/902,742, filed Nov. 11, 2013, 61/977,478, filed Apr. 9, 2014; 62/005,355, filed May 30, 2014; and 62/007,339, filed Jun. 3, 2014, all of which are incorporated by reference herein in their entireties.

BACKGROUND

For physicians and medical professionals, accessing systems for vessels and bodily cavities in patients have typically used various guidewire and catheter technologies. In some cases, the process requires the insertion of a series of mandrels or wires to increase the lumen diameter for the eventual passage of a larger bore instrument within the vessel. This technique can be referred to as "Dottering" or in the case of accessing the cervical canal and uterus, physicians will use a series of increasing diameter mandrels known as Hegar dilators. In the techniques described above, the methods involved pushing an object, mandrel, or device through the vessel to gain access to a desired region in the body. The result of pushing an object, mandrel, or device creates shear forces on the lumen wall. In some cases the shear forces can result in trauma, pain for the patient, or perforation.

In contrast, another access technology that has been used in prior art is referred to as an everting catheter. Everting catheters utilize a traversing action in which a balloon is inverted and with the influence of hydraulic pressure created by a compressible or incompressible fluid or media, rolls inside out or everts with a propulsion force through the vessel. Everting balloons have been referred to as rolling or outrolling balloons, evaginating membranes, toposcopic catheters, or linear everting catheters such as those in U.S. Pat. Nos. 5,364,345; 5,372,247; 5,458,573; 5,472,419; 5,630,797; 5,902,286; 5,993,427; 6,039,721; 3,421,509; and 3,911,927; all of which are incorporated herein by reference in their entireties. These are categorized as everting balloons and are for traversing vessels, cavities, tubes, or ducts in a frictionless manner In other words, an everting balloon can traverse a tube without imparting any shear forces on the wall being traversed. Because of this action and lack of shear forces, resultant trauma can be reduced and the risk of perforation reduced. In addition as a result of the mechanism of travel through a vessel, material and substances in the proximal portion of the tube or vessel are not pushed or advanced forward to a more distal portion of the tube or vessel.

In addition, as the everting catheter deploys inside out, uncontaminated or untouched balloon material is placed inside the vessel wall. In the inverted or undeployed state, the balloon is housed inside the catheter body and cannot come into contact with the patient or physician. As the balloon is pressurized and everted, the balloon material rolls inside out without contacting any element outside of the vessel. Another advantage of an everting balloon catheter is that the method of access is more comfortable for the patient since the hydraulic forces "pull" the balloon membrane through the vessel or duct as opposed to a standard catheter that needs to be "pushed" into and through the vessel or duct.

The method typically used by physicians for accessing the cervical canal in women requires the use of multiple instruments of increasing diameter. The physician will use a small uterine sound or small diameter probe or Hegar device for gaining initial entry into the uterus via the cervix. Ever increasing sizes of Hegars are used to stretch the cervical muscles until the desired internal diameter is achieved for the insertion of a secondary instrument such as an endoscope or other device. This process can be particularly difficult in some nulliparous, post-menopausal women with very small diameter cervical canals. A cervix could be difficult to traverse as a result of prior surgery, underlying stenosis, or other anatomical configuration or tortuosity that makes the passage of instruments or Hegar dilators difficult.

There are some cervical dilators that provide radial expansion to open the cervical canal to a greater internal diameter without the insertion of multiple instruments. All of these devices are predicated on first crossing or traversing the cervical canal prior to the step of radial expansion. Once traversed through the cervical canal, these devices use either mechanical means or the expansion of a balloon dilation member that is concentric on the exterior of the dilator probe. If the cervical canal is particularly tight or narrow, a small diameter probe or mandrel may be required to first cross the cervix and access the uterine cavity. As mandrels or instruments get smaller in diameter, the likelihood of perforation or a false passage increases. In any case, these cervical dilators require passage or crossing by the initial probe prior to any further radial expansion being performed.

Everting catheters have been described as dilatation catheters. Representative examples of dilating everting catheters include U.S. Pat. Nos. 5,364,345 and 4,863,440, both of which are incorporated by reference herein in their entireties.

Everting catheters have also been described with additional elements such as a handle for controlling instruments within an everting catheter. A representative example is U.S. Pat. No. 5,346,498 which is incorporated by reference herein in its entirety. Everting balloon catheters can be constructed with an inner catheter with an internal lumen or through-lumen (or thru-lumen). The through-lumen can be used for the passage of instruments, media, materials, therapeutic agents, endoscope, guidewires, or other instruments. Representative samples of everting catheters with through-lumens are in U.S. Pat. Nos. 5,374,247 and 5,458,573. In addition, everting catheters have been described with waists or a narrowing of the balloon diameter, such as in U.S. Pat. Nos. 5,074,845, which is incorporated by reference herein in its entirety.

Furthermore, infertility is a condition that affects 1 out of 8 couples in the US. One of the early treatments in the infertility regime is insemination. Intrauterine insemination or IUI is a very common procedure since it is in the early work up of an infertile couple. Most assisted reproductive clinics perform at least 3 IUI cycles before trying more expensive treatment options such as IVF. IUI cycles may be coupled with drugs to stimulate greater ovulation to improve the chances or likelihood of pregnancy. Sperm that is collected from the male is typically washed and prepared prior to an insemination through a catheter with the goal of providing a greater volume or amount of viable sperm in the uterine cavity and into the reproductive tract of the female.

As part of increasing the odds of getting pregnant, physicians have been using a variety of means of increasing both the amount of sperm and the duration sperm could be in the uterine cavity. To keep sperm from exiting the cervical canal after insemination, physicians have used rubber and silicone based cervical caps that are designed to fit over the exocervix as a sealing member. In practice, a physician will either inseminate the uterine cavity or fill the cervical cap with sperm and then fit over the cervix as a seal. The security of the cervical cap is not reliable and due to its size and bulk, not as comfortable for the patient. Typically a cervical cap will only be used by the patient within the physician's office for a predetermined amount of time. The overall objective of the cervical cap is to keep sperm in the uterine cavity for as long as possible without being expelled or spilling from the cervix due to gravity or contractions of the uterus. Ideally the sperm will migrate upward through the fallopian tubes to the fimbria where conception can occur if an oocyte from an ovary is present. Many clinical investigations have reported that, once through the fallopian tubes, sperm can travel throughout the peritoneal cavity and stay viable for many hours in situ. Equally, sperm can stay viable in a controlled environment or an incubator for many hours.

Another methodology for keeping sperm in the uterine cavity is done by use of a pump connected to a catheter within the uterine cavity. A pump that can be worn by the women or keep bedside is filled with sperm and is pumped through the catheter at a rate pre-set by the physician. For instance, the pump can be set to run for 2 to 6 hours at which sperm is pumped through the catheter and into the uterine cavity. The pump can be worn by the woman outside of the physician's office but patient mobility is limited due to keeping the integrity of the conduit and pump.

Also, when delivering the reproductive material, such as an embryo, into the uterine cavity, vacuum effect can unintentionally remove the reproductive material from the uterine cavity. In existing systems, when the transfer catheter is retracted from a second outer or guiding catheter (e.g., the "inner" catheter), the retraction produces vacuum pressure within the uterine cavity. This vacuum pressure is created in the uterine cavity by the removal and backward movement of the transfer catheter within the inner catheter. After the embryo transfer is completed, an embryologist may inspect the transfer catheter to verify that the embryos or reproductive material was indeed deposited in the uterus and not pulled back into the transfer catheter because of the vacuum effect. The same procedure may be done for the outer catheter once this catheter is removed.

Further, incontinence is a prevalent clinical and social issue that primarily affects women. Various publications estimate the percentage of women with urinary incontinence from 15 to 30% in the over 60 age group. The amount spent treating incontinence ranges from $3 to 5 B annually in the US. Urinary Incontinence is one of the 10 most common chronic conditions in the US with over 15 M women diagnosed in the US alone. Most feel that this number is under-reported. The choice of therapeutic options has limited reimbursement and many of the techniques lack consistent data. As an example, invasive approaches in women include suspensions of the bladder neck, collagen injections, and RF remodeling. Incontinence is a multi-factorial disease condition and patient satisfaction with many invasive techniques is poor. For patients, surgery is the last preferred resort. Noninvasive techniques include biofeedback and Kegel exercisers. These techniques improve the muscle tone in the patient's pelvic floor but they rely on patient compliance to be effective. Less invasive options involve mechanical pressure devices such as pessaries, urethral catheters or inserts, and patches over the urethral opening. Most incontinence money is expended on purchase of absorbent products. Due to the social stigma, many patients are reluctant to seek advice and many patients decline surgical and less invasive options. Consequently, male and female incontinence patients rely on sanitary pads and the restrictions that the presence of bulky, wet pads imposes on their daily lives.

In some patients, a urethral insertable device for sealing is the preferred method for managing their incontinence. These inserts are designed for single use and are self-applied. Typically they rely on the measurements of urethral length for insertion and balloon inflation.

Urethral inserts are plugs that typically incorporate a balloon mechanism to create a seal in the urethra or bladder. For voiding, the balloon is deflated. These devices have been described previously in the art including U.S. Pat. Nos. 5,090,424; 5,483,976; 5,724,994; 5,752,525; and 5,769,091 all attributed to Simon et al. Additional art is found in U.S. Pat. Nos. 5,806,527; 6,449,060; 6,926,708; EP 0900058 B1, and EP 1365713 B1. U.S. Pat. No. 5,927,282 to Lenker et al describes an adhesive patch for covering and sealing the urethral opening and sealing the external opening to the urethra.

Further art includes U.S. Pat. No. 5,662,582 which describes an everting urethral plug with an invaginating balloon mechanism. Everting balloons describe an action in which a balloon is inverted and, with the influence of hydraulic pressure created by a compressible or incompressible fluid or media, rolls inside out or everts with that propulsion force. Everting balloons have been referred to as rolling or outrolling balloons, evaginating membranes, toposcopic catheters, or linear everting balloons. These are all categorized as everting balloons due to their property of traversing vessels, cavities, tubes, or ducts in a substantially frictionless manner Everting balloons can traverse a tube without imparting any significant shear forces on the wall being traversed. Because of this action and lack of shear forces, material and substances in the proximal portion of the tube or vessel are pushed or advanced forward to a more distal portion of the tube or vessel. For example for urethral everting balloons, potentially infectious substances from the vagina, urethral openings, or the hands of the patient, are not in contact with the everted balloon that resides in the urethra. In contrast, urethral plugs and inserts in use currently have a propensity of urinary tract infections which may be a result of the lack of cleanliness of the device that resides in the urethra or bladder.

This methodology would be more widely adopted if the inserts were more comfortable while wearing, had less of a foreign body sensation, and were easier to use or insert. More significantly, many patients who are insert users complain of higher incidence of urethral infection and soreness at their urethra and groin region, especially with increased activity, which is the ideal time the user would want the insert to operate properly.

For a patient, being able to insert a device within their own urethra is not easy and the act itself is unnatural for the patient. Training by a nurse or physician is required for a patient to master the technique. Since the inserts used today require pushing a device through the urethra, the urethral passageway could become sore or tender after repeated insertions.

Current urethra inserts are typically sized to match the length of the patient's urethra, not as a "one size fits all."

Current inserts need to create a balloon seal at the bladder coupled with a compressive force at the urethral opening. Thus the insert length is calculated by sounding the length of the urethra by a probe or via ultrasound measurement. The calculation is designed to hold the balloon taut against the opening of the bladder and the compressive force of the external portion of the insert of the opening of the urethra. Hence it is understandable that the presence of a relatively stiff device that is keeping the opening of the bladder tight against the urethral opening can create an uncomfortable feeling for the patient, especially a patient that is active and mobile.

Furthermore, urinary protection and voiding could occur 3 to 7 times a day, a high cost device would not be acceptable to most patients or would limit the device usage to only the most socially challenging events.

SUMMARY OF THE INVENTION

An everting balloon system is disclosed. The everting balloon system can be used for insemination, urinary incontinence, dilation of a body lumen, for access and sealing within a body cavity, or combinations thereof. The system can have automatic disengagement. The system can have a handle for insertion. The system can have a motorized air pump. The system can have inner and outer catheters that can automatically disengage upon everting.

The everting balloon system can have deflation and removal mechanisms of a device that can be worn by a mobile patient in a body lumen (e.g., cervical canal or urethra) and be deflated and removed by the patient.

The everting balloon system can have an intubating base with a locking balloon that can activate upon pressurization. The system can be a compact, low profile unit used in vivo. The system can be single use and disposable. The system can be non-irritation and non-infection causing.

The everting balloon system can be used for cervical access and dilation. The everting balloon system can have a system handle mechanism that can enable a one-handed operating technique by the user. The one-handed operating technique can include advancement and pressurization of the everting balloon membrane within the control of the user with one hand.

The everting balloon system can be used for insemination and can seal the cervix for a duration of time for the deposition of sperm and to allow for mobility for the patient. The everting balloon system can have a decoupling mechanism configured to decouple the outer catheter and inner catheter while maintaining hydraulic pressure in an everting balloon. The system can deflate and removal the everting balloon concurrently.

The system can be used to place or deliver fallopian tube inserts (i.e., intratubal inserts, such as the Essure device from Bayer Corporation) in fallopian tubes. The system can access the intramural and isthmic portions of the fallopian tube. All or part of the everting catheter system can be loaded into a hysteroscope and placed with direct endoscopic visualization.

The everting catheter system can be a selective fallopian tube catheter with a curved distal end section and angled ball tip. This configuration can be performed by ultrasound or radiographic visualization.

One or more fallopian tube occluding devices (e.g., the Essure device) can be loaded into the everting balloon system, for example, in the through lumen of the inner catheter. Once fully everted and placed into the fallopian tube, the everting balloon system, such as the inner catheter, can be withdrawn from the fallopian tube while leaving the fallopian tube occluding device in the fallopian tube. Once the everting balloon system is withdrawn from the fallopian tube, the fallopian tube occluding can be deployed (e.g., device anchors such as coils can be extended, or a resilient porous matrix can expand to friction fit the tube lumen). Once the fallopian tube occluding device is deployed, a central guidewire can be removed from the fallopian tube. The procedure can be repeated for the contralateral fallopian tube.

The everting balloon system can be used to access the bladder, ureters, kidneys, or combinations thereof. Devices, tools, instrumentation, endoscopes, drugs, therapeutic agents, sampling devices (brushes, biopsy, and aspiration mechanisms), or combinations thereof can be delivered through the inner catheter lumen to the target site.

BRIEF DESCRIPTION OF THE DRAWINGS

FIG. 2A illustrates a variation of the everting balloon system in a fully everted configuration.

FIG. 2B is a cross-sectional view of a variation of the system handle.

DETAILED DESCRIPTION

Figure 1A:
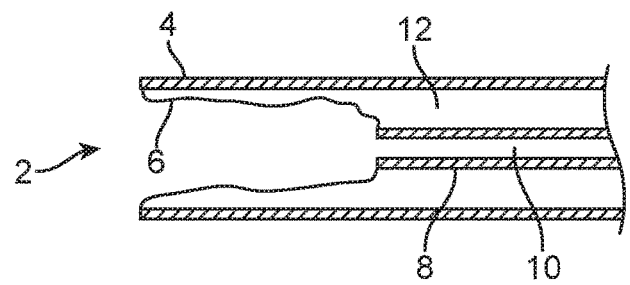
FIGS. 1A through 1E are longitudinal cross-sectional views of the distal end of a variation of a method for using the everting balloon system.

An everting balloon system 2 (also referred to as an everting catheter system) that can be used to traverse a vessel, such as the cervical canal is disclosed. The everting balloon system 2 can be used to access the uterine cavity via the cervix. The cervical canal is a single lumen vessel that can stretch or dilate. The everting balloon system 2 can have a control system that can be operated with one hand.

FIGS. 1A through 1E illustrate that an everting catheter system 2 can have a radially outer catheter 4, a balloon membrane 6, and a radially inner catheter 8. The inner catheter 8 can have an inner catheter lumen 10 (e.g., a through-lumen). The distal end of the inner catheter lumen 10 can be open or closed. The inner catheter 8 can have the inner catheter lumen 10 or be a solid rod or flexible mandrel. The everting balloon system 2 can have a media volume 12. The media volume 12 can be the contiguous open volume between the inner catheter 8 and outer catheter 4 that is proximal to the balloon membrane 6. A radially outer terminal perimeter of the balloon membrane 6 can be attached to the distal terminal end of the outer catheter 4. A radially inner terminal perimeter of the balloon membrane 6 can be attached to the distal terminal end of the inner catheter 8. The everting balloon system 2 can be made without an inner catheter 8, for example with the balloon membrane 6 extending proximally out of the working area to a control device (e.g., a pump).

FIG. 1A illustrates that the everting catheter system 2 can be in an unpressurized configuration. The media volume 12 can be uninflated and unpressurized. The balloon membrane 6 can be slack.

Figure 1B:
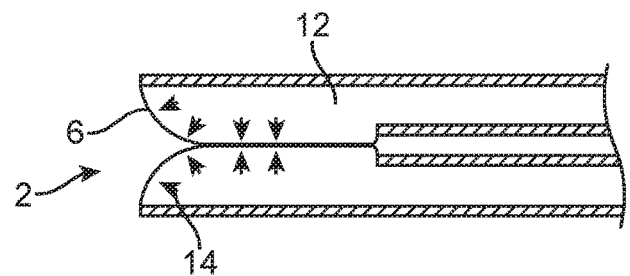

FIG. 1B illustrates that that everting catheter system 2 can be in a pressurized and uneverted configuration. A pressurization device, such as a pump, for example at the proximal end of the everting catheter system 2 can be in fluid communication with the media volume 12. The pressurization device can deliver a fluid media, such as a pneumatic gas or hydraulic liquid media (e.g., saline, water, air, carbon dioxide, or combinations thereof), at a media pressure 14 to the media volume 12. The media pressure 14 in the everting balloon 2 can be from about 2 to about 5 atmospheres of pressure when in the everted configuration and higher media pressures 14 from about 5 atmospheres to 10 atmospheres are possible, for example, to provide greater everting capability for more difficult or stenotic passageways in the body.

The balloon membrane 6 can inflate and be in tension. The balloon membrane 6 can block the distal port of the inner catheter lumen 10.

Figure 1C:
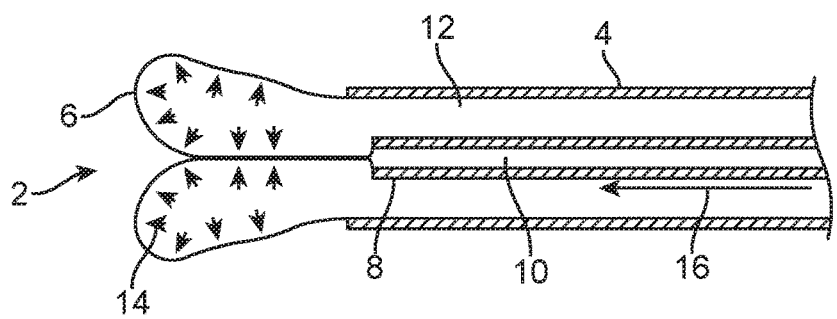

FIG. 1C illustrates that the everting catheter system can be in an inflated and partially everted configuration. The inner catheter 8 can be translated distally, as shown by arrow 16, with respect to the outer catheter 4, and out of the outer catheter 4. The distal terminal end of the inner catheter 8 can be proximal of the distal terminal end of the balloon membrane 6. The distal terminal end of the inner catheter 8 can be proximal or terminal of the distal terminal end of the outer catheter 4. The balloon membrane 6 can block the distal port of the inner catheter lumen 10 or can be open allowing fluid communication between the inner catheter lumen 10 and the target site.

Figure 1D:
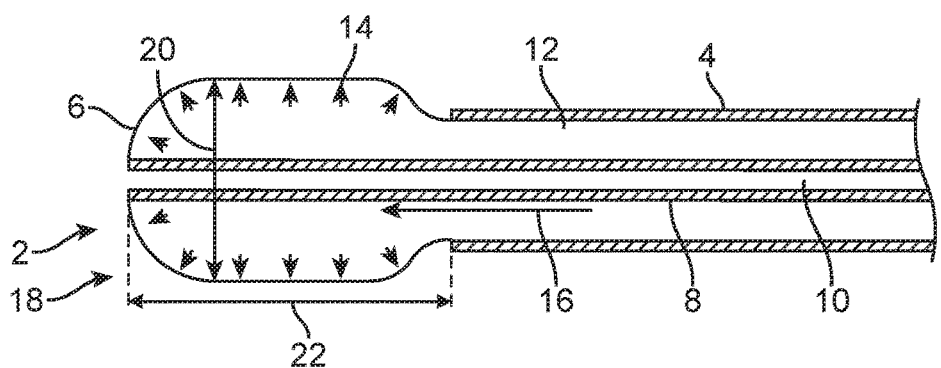

FIG. 1D illustrates that the everting catheter system can be in an inflated, fully everted, and fully distally extended configuration. The inner catheter 8 can be translated distally, as shown by arrow 16, with respect to the outer catheter 4 until the distal terminal end of the inner catheter 8 is longitudinally beyond or co-terminal with the distal terminal end of the balloon membrane 6. The distal port of the inner catheter lumen 10 can be unobstructedly accessible and in fluid communication with the target site.

In the fully inflated configuration, the balloon membrane 6 can form an inflated everting balloon 18. The everting balloon 18 can have a balloon outer diameter 20 and balloon length 22 in the inflated and fully everted configuration.

The balloon outer diameter 20 can be from about 2 mm to about 20 mm, more narrowly from about 2 mm to about 7 mm, for example about 5 mm. The outer diameter can be constant or vary along the length of the everting balloon 18. For example, for use in the cervical canal, the most proximal portion of the everting balloon outer diameter 20 could be configured with a smaller outer diameter than the remainder of the everting balloon membrane 24. As an example, the first proximal portion of the everting balloon 18 can have a smaller balloon outer diameter 20 such as from about 2 mm to 4 mm for a length of from about 5 mm to about 10 mm from the distal terminal end of the outer catheter 4, and the remainder of the length (e.g., from about 4 cm to about 7 cm along the everting balloon 18) of the everting balloon 18 can have a balloon outer diameter 20 from about 4 mm to about 7 mm The outer diameter of the proximal end of the everting balloon 18 can have a consistent balloon outer diameter 20, for example for delivery in the urethra, of from about 3 mm to about 6 mm, and the distal-most outer about 2 cm to about 3 cm of the everting balloon 18 can have a balloon outer diameter 20 from about 10 mm to about 20 mm, for example to create a seal with and anchor in the bladder.

The exterior surface of the balloon membrane 6 can be configured with ridges, projections, bumps, grooves, and additional surface or mechanical features, or combinations thereof, for example for increased friction or holding power within the vessel.

The everting balloon length 22 can be from about 2 cm to about 31 cm, more narrowly from about 2 cm to about 25 cm (e.g., for use in a male urethra), yet more narrowly from about 2 cm to about 7 cm, yet more narrowly from about 3 cm to about 6 cm, for example about 4 cm, about 7 cm, about 15 cm and about 30 cm.

Figure 1E:
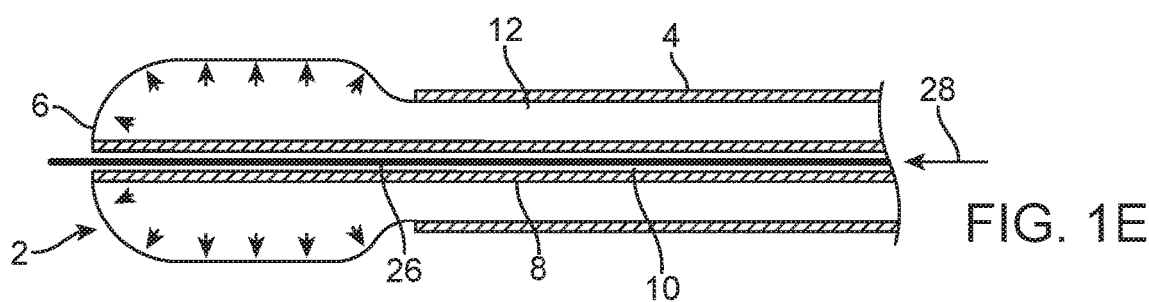

FIG. 1E illustrates that the everting catheter system can be in an inflated and partially or fully everted configuration. A tool 26, liquid, gas, or combinations thereof can be translated, as shown by the arrow 28, through the inner catheter lumen 10, out of the distal port of the inner catheter lumen 10 and into the target site. The tool 26 can be a biopsy tool, a scope, a sonogram probe, a plug, a cauterization tool, or combinations thereof. Suction can be applied from the proximal end of the inner catheter lumen 10, and to the target site, for example removing debris from the target site through the inner catheter lumen 10.

To retract and reposition or remove the balloon membrane 6, the inner catheter 8 can be pulled proximally to pull the balloon membrane 6 back within the outer catheter 4. The balloon membrane 6 can be deflated or have media pressure 14 reduced and the entire system can be withdrawn from the target site.

FIG. 2 illustrates that the everting balloon system 2 can have a system handle 30. The system handle 30 can have a system handle connector 32. The system handle 30 can be attached to the outer catheter 4 and the inner catheter 8, for example at the system handle connector 32. The system handle connector 32 can be removably attached to the outer catheter 4. For example, the outer and inner catheters 4, 8 and balloons can be detached from the system handle 30 and replaced. The system handle 30 can be sterilizable. Media (e.g., liquid or gas) delivered by the system handle 30 can be filled into the system handle 30 before attaching or replacing the catheters and balloons.

The system handle 30 can have a rigid system handle case 34 and a rigid pump lever 36 rotatably attached to the system handle 30 case at a pump lever axle 38.

The system handle 30 can have an inlet port 40. The everting balloon system 2 can have a pressurization source. The pressurization source can have a flexible liquid reservoir 42 or fluid supply container or bag. The fluid bag can be filled with a hydraulic and/or pneumatic fluid.

The inlet port 40 can be a female luer fitting and connection. The inlet port 40 can be in fluid communication through an inlet-reservoir channel 44 with the flexible reservoir 42. The liquid reservoir 42 can be between the rigid pump lever 36 and a rigid system handle case 34. The inlet port 40 can extend out of the proximal end of the system handle case 34. The inlet port 40 can be configured to attach to a liquid source (e.g., a hose, tube, or supplemental reservoir configured to deliver the liquid through the inlet port 40 and to the liquid reservoir 42). The inlet port 40 can have a proximal check valve or one-way valve configured to allow flow to the liquid reservoir 42 and prevent backflow (e.g., proximal flow from the liquid reservoir 42 and out the inlet port 40).

The liquid reservoir 40 can be in one-way (e.g., via a check valve) or two-way fluid communication with the media volume 12.

When the liquid reservoir 42 contains liquid, the pump lever 36 can rotate away from the system handle case 34, as shown by pump lever rotation arrows 46, as the liquid reservoir 42 inflates. The pump lever 36 can be rotated toward the system handle case 34 to compress the liquid reservoir 42, for example, forcing liquid from the liquid reservoir 42 and into the media volume 12 of the everting balloon 18.

The pump lever 36 can provide a pumping (e.g., suction) action to supply aspiration to withdraw liquid from the media volume 12 of the everting balloon 18. A spring within the lever can facilitate the pumping action of the lever to open the lever (not shown) for each compression.

The system handle 30 can have an advancement slide 48. The advancement slide 48 can be proximally and distally translatable, as shown by arrow 50, with respect to the system handle case 34. The advancement slide 48 can be configured to translate the inner catheter 16 with respect to the outer catheter 4. For example, pushing the advancement slide 48 distally can push the inner catheter 8 distally with respect to the outer catheter 4 and evert the everting balloon 18. Pulling the advancement slide 48 proximally can pull the inner catheter 8 proximally with respect to the outer catheter 4 and retract the everting balloon 18. The advancement slide 48 can have gear wheels, ratchets with racks, and rotating advancement screws.

The advancement button can be an advancing ratchet or a roller wheel that is geared into or with the inner catheter 8 to allow for translation of the inner catheter 16.

With one hand, the physician can advance the inner catheter 8, evert the everting balloon 18, traverse the cervical canal with the everting balloon 18, and access the uterine catheter through the inner catheter lumen 10.

The fluid reservoir 42 can be pressurized prior to placement of the distal tip of the outer catheter 4 at the cervix. The fluid reservoir 42 can has a proximal check or one-way valve on the proximal portion of the handle. The proximal check valve is the connection point for the physician to pressurize the system. The distal portion of the fluid bag can be attached to a distal pressure check valve 52 that can open when pressure from the fluid bag is at or above a distal check valve limit pressure, for example about 1 atmosphere of pressure from the liquid reservoir, and then deliver liquid and pressure from the liquid reservoir 42 to fill and pressurize the media volume 12 of the catheters and everting balloon 18. The distal pressure check valve 52 can be a one-way valve allowing hydraulic or pneumatic fluid or media to go from the fluid reservoir 42 to the media volume 12 of the catheters and everting balloon 18. Higher and lower atmosphere pressure ratings from 1 atmosphere are also possible for the distal pressure check valve 52 such as from about 0.5 atmospheres to about 2 atmospheres.

During pressurization of the fluid reservoir 42 (e.g., by pumping with the pump lever 36 or from the inlet port via the proximal check valve 54), pressures greater than a reservoir limit pressure (e.g., 1 atmosphere) of the distal pressure check valve 52 can open the distal pressure check valve 52 and allow fluid media to flow from the liquid reservoir 42 into the media volume 12 of the catheters and everting balloon 18. The pressurization in the media volume 12 of the catheters and everting balloon 18 can unroll and evert the everting balloon 18 under hydraulic force. Excess media can remain in the fluid reservoir 42 after the everting balloon 18 fully everts.

The distal pressure valve 52 can be connected to a three-way connector 56 (e.g., Y-connector or T-connecter) that has a hemostasis valve 58, for example a Touhy-Borst valve. Thus the fluid reservoir 42 can stage or hold additional potential hydraulic pressure to be stored in the system for the user (e.g., physician) to use as needed by rotating the pump lever 46 without a change of hand position or the use of a second hand.

The inner catheter 8 can extend through the three-way connector 56. The inner catheter 8 can translate (i.e., advance and retract) through the three-way connector 56 while maintaining a seal (i.e., without the media volume 12 of the catheters or everting balloon 18 losing pressure). The inner catheter 8 (e.g., if a solid rod or mandrel) can be configured to withstand hydraulic pressures of up to about 5 atmospheres or up to about 10 atmospheres during the everting process and translational (e.g., advancement, retraction, tensile, compression, or combinations thereof) forces of up to about 2 pounds or up to about 5 pounds without deformation. As an example, during the everting process the inner catheter 8 with an inner catheter lumen 10 (e.g., a through lumen) could withstand media pressures 14, tensile and compressive forces, and rotational forces as the everting balloon membrane 6 traverses curved or tortuous anatomy, to allow for the passage of an instrument, catheter, media, or materials within the through lumen. Movement of the advancement button on the handle moves the inner catheter 8 within the three-way connector 56 and through the outer catheter 4. The everting balloon 18 can then evert and roll out of the outer catheter 4 and traverse the target site (e.g., the cervical canal).

After accessing the target site, for example, the user can activate the pressure release control 60 to release or reduce the pressure from the media volume 12 thereby deflating or reducing the outer diameter of the everting balloon 18, and/or manually withdraw the everting balloon 18 and inner catheter 8 by retracting the advancement slide 48 or pulling the system handle 30 proximally, and therefore the remainder of the system.

Once the biological lumen to be traversed (e.g., the cervical canal, or urethra) is traversed by the everted balloon 18, the everting balloon system 2 can increase the pressure in the everting balloon 18, for example increasing the diameter of the everting balloon 18, or while maintaining a constant diameter everting balloon 18 (e.g., for a fiber-reinforced everting balloon 18 or a balloon membrane 6 constructed from a less distensible material). The pump lever 36 can be compressed to increase pressure in the fluid reservoir 42 builds and exits the distal pressure check valve 52. The proximal check valve 54 can prevent or minimize the fluid media (e.g., pneumatic or hydraulic pressure) from leaking or bleeding in the proximal direction and out of the inlet port 40.

The user can rotate the pump lever 36, for example increasing the pressure in the fluid reservoir 42, the media volume 12, and the everting balloon 18. The balloon outer diameter can then increase, further pushing open the diameter of the biological lumen. For example, the everting balloon 18 can dilate the cervix and cervical canal. Tools such as endoscopes, instruments, Hegars, other devices to increase the diameter of the cervix further, or combinations thereof, can then be inserted into the dilated cervical canal concurrent with the everting balloon system 2 being located in the cervical canal or subsequent to the everting balloon system 2 being withdrawn from the cervical canal.

The pump lever 36 can deliver tactile feedback to the user indicating the pressure of the everting balloon 18. The everting balloon system 2 can have a pressure gauge indicating the pressure in the media volume 12, such as in the liquid reservoir 42 and/or the media volume 12 in the catheters and everting balloon 18.

The system handle 30 can have a pressure release control 60, such as a toggle lever or knob. The pressure release control 60 can release fluid from the liquid reservoir 42 and/or media volume 12 of the catheters and everting balloon 18.

The pressure release control 60 can be connected to the hemostasis valve 58. The hemostasis valve 58 can have a seal or sealing gasket. The pressure release control 60 can be configured to open and close the sealing gasket by rotating the sealing cap, or open a connection to a separate drainage tube (not shown) in fluid communication with the media volume 12.

The pressure release control 60 can be on the handle 30 positioned by the user's thumb position, distal to and collinear with the movement of the advancement slide 48. The pressure release control 60 can be operated by the same hand as the user is operating the advancement slide 48 and pump lever 36.

The user can perform the following operations of the everting balloon system 2 with a single hand (e.g., without their other hand or another operator) without a change of hand position:

a. pressurize the liquid reservoir 42;
b. position or place the distal end of the everting balloon system 2 at the patient's cervix;
c. control the everting balloon system 2 position throughout use;
d. advance the inner catheter 8 and balloon membrane 6;
e. increase the diameter of the everting balloon 18 by pumping additional hydraulic pressure from the fluid reservoir 42;
f. retract the inner catheter 8 and balloon membrane 6; and
g. activate the pressure release control 60 to remove or release pressure from the everting catheter system.

Structurally, the buttons and actuators to enable these functions can be positioned on the handle to allow for the operator to manipulate these features without a change of hand position or requiring the use of the other hand. For instance, advancement and retraction of the inner catheter 8 can be performed by a slide mechanism or gear wheels that are located on the upper side of the handle approximately 4 inches from the proximal end of the handle or handle grip. Levers and ratchet mechanisms can be located on the lower or underneath side of the handle at a distance of from about 2 inches to about 4 inches from the proximal end of the handle grip. Additional actuators can be placed on the lateral sides of the handle grip from about 3 inches to about 4 inches from the proximal end of the handle grip or on the upper or lower portions of the handle grip from about 3 inches to about 4 inches from the proximal end. The button and actuator position can be palpable for the operator without requiring visual confirmation, thereby allowing the user to maintain eye contact with the patient or visualization source such as an endoscopic monitor or ultrasound image.

During the use of the everting balloon system 2, the user can utilize their other hand for handling an ultrasonic probe, a tenaculum (e.g., if the cervix is difficult to access by anatomical reasons or is severely retroverted or anteverted), stabilizing the patient or other instruments, or combinations thereof.

Figure 3A:
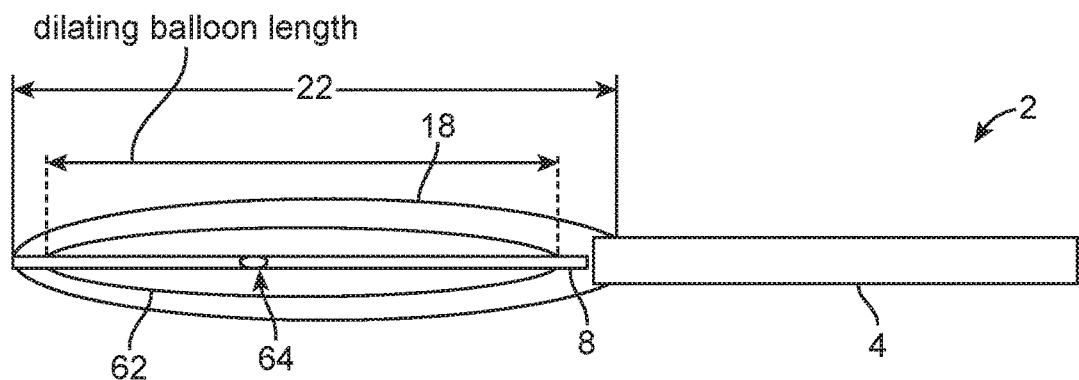
FIG. 3A illustrates a variation of the distal end of the everting balloon system with the dilating balloon in a less than fully inflated configuration.

FIG. 3A illustrates that the inner catheter 8 can be attached to a dilating balloon 62 or inner catheter balloon. The dilating balloon 62 can be radially inside of the everting balloon 18. The distal end and the proximal end of the dilating balloon 62 can be attached and sealed to the inner catheter 8. The inner catheter 8 can have a dilating balloon port 64 longitudinally within the dilating balloon 62. The dilating balloon port 64 can be in fluid communication with a fluid pressure source at the proximal end of the everting balloon system 2, for example in or attached to the system handle 30. The dilating balloon 62 can be inflated and deflated through the dilating balloon port 64.

The dilating balloon 62 can be more, the same, or less compliant than the everting balloon 18. The everting balloon 18 wall can be thicker, thinner, or the same thickness as the dilating balloon 62 wall. The everting balloon 18 can be made from one or more polymers including silicone, urethane, rubber, latex, polyethylene, polyolefin, irradiated polyolefin combined with ethylene vinyl acetate, co-polymers such as polyether block amide (PEBA, also known as Pebax), a fiber-reinforced polymer, PET, nylon, or combinations thereof. The dilating catheter can be made from any of the materials mentioned for the everting balloon 18.

The everting and/or dilating balloon membrane 6 can have a thickness from about 0.001 in to about 0.004 in.

The everting and/or dilating balloon 18, 62 can be internally coated with a lubricious material such as silicone oil, mineral oil, other lubricant, or combinations thereof. The lubricous coating can reduce the friction within the balloon during eversion.

The exterior of the everting and/or dilating balloon 18, 62 can be smooth, for example the balloon can be made by tubing extrusion. The balloons can be blow molded. For example, the exterior surface of the balloon can have ridges or other surface protrusions, for example to increase friction or holding forces in the target body lumen (e.g., cervical channel or urethra). The outer diameter of the balloons can vary dimensionally. For instance, the most distal portion of the everting balloon 18 can be manufactured with a larger outer diameter to accommodate larger vessel sizes or inflation that can extend into the bladder.

During use, the everting balloon 18 can pull the inner catheter 8 into the endocervical canal. When the everting balloon 18 is deployed into the cervical channel, the dilating balloon 62 can be positioned in the cervical channel.

Figure 3B:
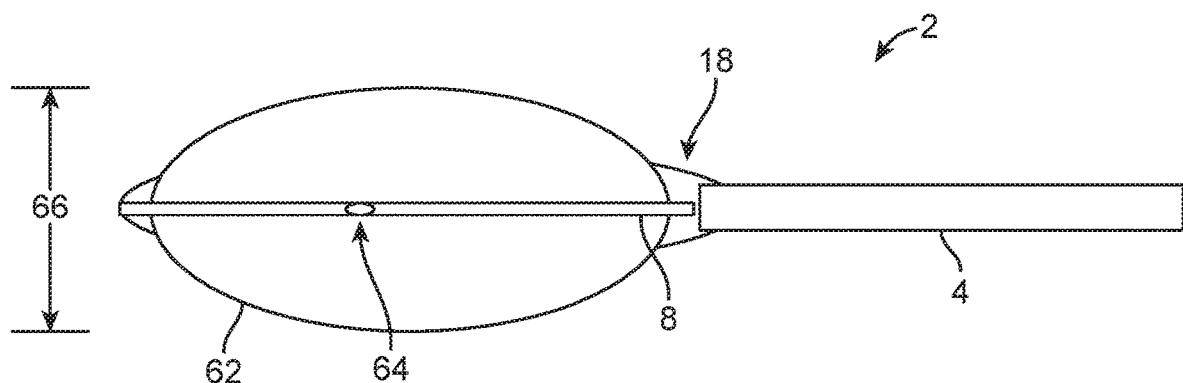
FIG. 3B illustrates a variation of the distal end of the everting balloon system with the dilating balloon in a fully inflated configuration.

FIG. 3B illustrates that the dilating balloon 62 can be inflated by delivering pressurized fluid through the dilating balloon inflation port 64. The dilating balloon 62 can expand inside of the everting balloon 18. The dilating balloon 62 can inflate to a dilating balloon diameter 66.

The dilating balloon 62 can have a predetermined or molded size and shape. For example, the dilating balloon 62 can have a dilating balloon diameter 66. For example, the maximum dilating balloon diameter 66 or maximum everting balloon diameter can be from about 2 mm to about 12 30 mm, and for some applications, up to about 20 mm in diameter (e.g., for use in a cervix), and more narrowly from about 2 mm to about 10 mm (e.g., for use in a urethra), more narrowly from about 6 mm to about 12 mm, yet more narrowly from about 2 mm to about 7 mm (e.g., for use in a urethra), yet more narrowly from about 3 mm to about 4 mm (e.g., for use in a male urethra). The dilating balloon 62 can inflate to a preset outer diameter. (The dilating balloon outer diameter 66 can be equal to or less than the dilating diameter needed for the body lumen, such as the cervix.) The everting balloon 18 can have a maximum everting balloon diameter equal to or less than the maximum dilating balloon diameter 66.

The dilating balloon 62 can be inflated to the same or a higher pressure than the everting balloon 18. For example, the dilating balloon 62 can have a dilating balloon pressure from about 4 atmospheres to about 12 atmospheres of pressure, and up to about 20 atmospheres of pressure, for example for disrupting a pathological stenosis or condition within a bodily lumen.

When the dilating balloon 62 is inflated, the everting balloon 18 can stretch due to the expanding dilating balloon 62 to the dilating balloon diameter 66. The inflation media within the everting balloon 18 can remain inside the balloon or be withdrawn before, during, and/or after inflation of the dilating balloon 62. Due to the frictional forces of the everting balloon membrane 6 on the bodily lumen in the everted state, for example, the everting balloon membrane 6 can serve to maintain the position of the dilating balloon 62 during the dilation process without unintentional advancement or retraction of the system within the bodily lumen during the dilatation process.

The dilating balloon 62 can inflate and tear or break the everting balloon 18 as the everting balloon diameter expands beyond the strain limit for the everting balloon 18. The inflation media within the everting balloon 18 can remain inside the balloon or be withdrawn before, during, and/or after inflation of the dilating balloon 62, for example exiting the everting balloon 18 can exit when the everting balloon 18 tears open.

The everting balloon 18 can break or tear along an intentional line upon the inflation of the dilating catheter. For example, the everting balloon 18 can be torn by a mechanical instrument on or within the outer catheter 4, a sharp implement on the proximal portion of the inner catheter 8 that becomes active upon full eversion and inflation of the dilating balloon 62, and/or further advancement of the inner catheter 8 that disengages the attachment or bond between the everting balloon 18 and the inner catheter 8 on the distal end of the inner catheter 8. The tearing or splitting of the everting balloon 18 can be done be weakening the everting balloon 18 with a mechanical indentation or seam on the balloon membrane 6 that splits upon reaching a specific strain limit, such as along a helical line, lateral line, longitudinal line, or combinations thereof. The everting balloon membrane 24 can be manufactured with increased longitudinal axial orientation of the molecular structure by tensioning or expanding the membrane along the longitudinal axis of the balloon during the balloon forming process which can promote a longitudinal break if the everting balloon membrane 24 splits or tears. A radial tear in the everting balloon 18 can be promoted by manufacturing the balloon membrane 6 with greater radial orientation of the molecular structure by radially expanding or tensioning the balloon membrane 6 during the balloon forming process.

The system handle 30 can hold the inflation media to be delivered to and from the everting balloon 18 and the dilating balloon 62. The inflation media can be in the liquid reservoir 42 (e.g., the fluid bag or a syringe piston). The inflation media can be delivered, for example via valves, to the dilation balloon after the inflation and eversion of the everting balloon 18. The system handle 30 can have gear wheels or a ratchet configured to advance the inner catheter 8. The outer catheter 4 can extend about 25 cm distal to the system handle 30. The system handle 30 and actuators can inflate the everting balloon 18 and dilating balloon 62 from control with one hand.

The dilating balloon 62 can be positioned into and dilate the cervix.

Figure 4A:
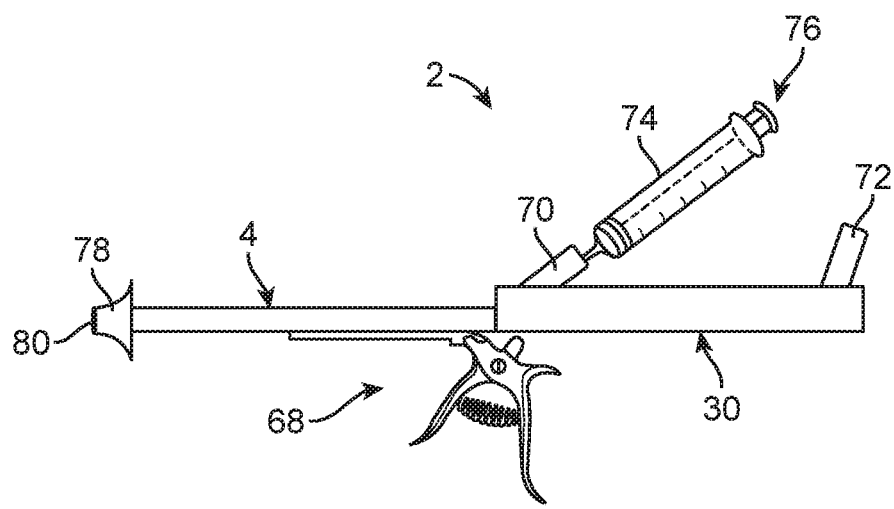
FIG. 4A illustrates a variation of the everting balloon system with a syringe in an attached, but not yet deployable configuration.
Figure 4B:
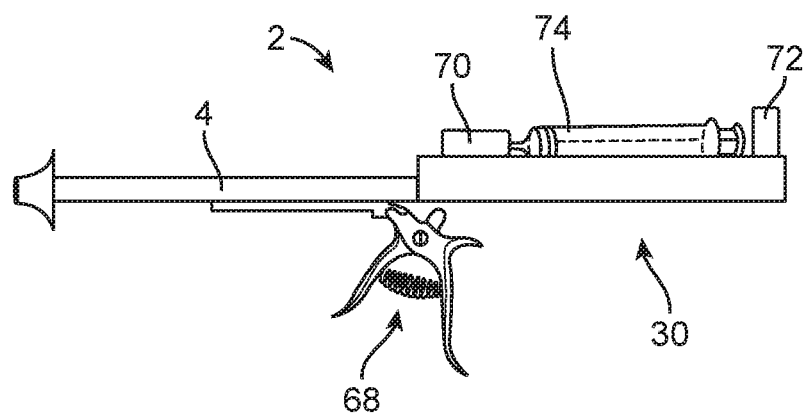
FIG. 4B illustrates a variation of the everting balloon system with the syringe in an attached and deployable configuration.
Figure 4C:
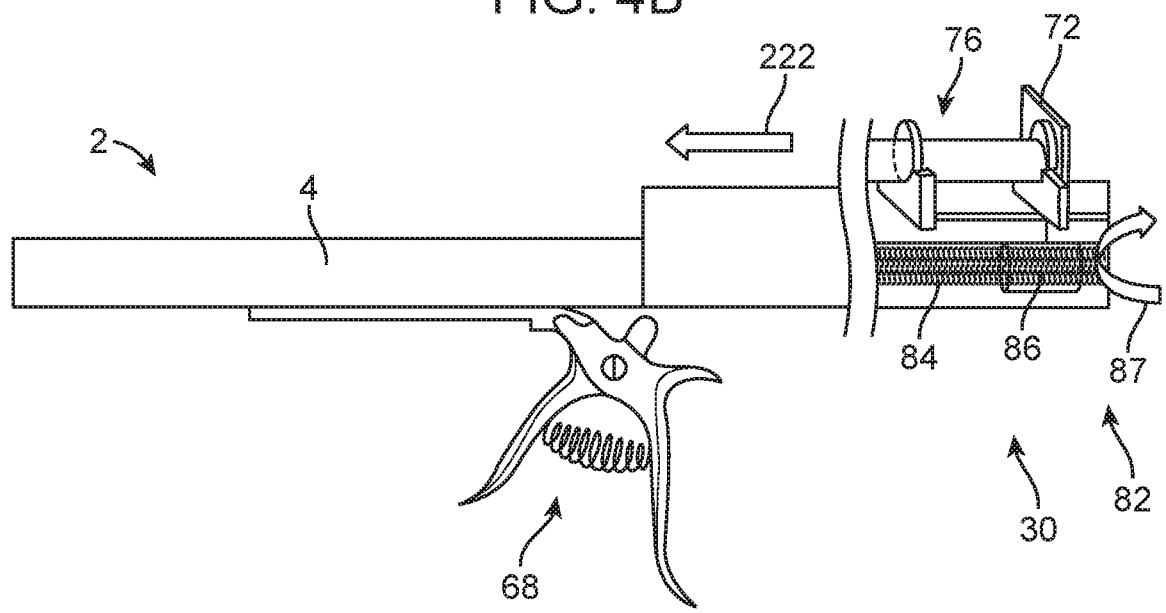
FIG. 4C illustrates a variation of the everting balloon system of FIG. 4B with the plunger driver shown in cut-away.

FIGS. 4A through 4C illustrate that the inner catheter 8 can be in a fully retracted position inside of the outer catheter 4.

FIG. 4A illustrates that the system handle 30 can have a pump lever 36, such as a ratchet handle 68, a syringe connector 70, and a plunger drive plate 72. The ratchet handle 68 can have a finger grip, trigger, lever, pump mechanism, or combinations thereof. The fluid reservoir can be a syringe 74. The syringe 74 can have a volume from about 5 cc to about 20 cc, for example about 5 cc or about 20 cc. An open distal port of the syringe can be attached to and in fluid communication with the syringe connector 70. The syringe connector 70 can have the distal pressure valve 52. The syringe connector 70 can be rotatably attached to the system handle case 34. The syringe 74 can have a plunger 76 longitudinally translatable with the remainder of the syringe 74. The syringe 74 can be filled with any media disclosed herein, such as saline, air, gas, or combinations thereof. The liquid reservoir 42 can have two separate syringes 74, each attached to and in fluid communication with the same or different syringe connectors 70. For example, a first syringe can be in fluid communication with the everting balloon 18, and the second syringe can be in fluid communication with the dilation balloon 62.

The syringe 74 can be locked to the syringe connector 70.

The outer catheter 4 can have an outer catheter distal tip 78. The outer catheter distal tip 78 can be, for example, an atraumatic tip such as an acorn tip or stop. The outer catheter distal tip 78 can be configured to prevent insertion of the outer catheter 4 too far into the target biological lumen (e.g., the endocervix).

The outer catheter distal tip 78 can have an outer catheter distal port 80. The outer catheter distal port 80 can be large enough to allow the inner catheter 8 and balloons to pass through.

FIG. 4B illustrates that the syringe connector 70 and syringe 74 can rotate, as shown by the arrow, so the longitudinal axis of the syringe 74 can be parallel or collinear with the longitudinal axis of the outer catheter 4. The syringe connector 70 can be angularly fixed with respect to the rest of the system handle 30. The plunger drive plate 72 can be rotated and/or translated to contact or almost contact the proximal end of the syringe plunger 76.

FIG. 4C illustrates that the system handle 30 can have a plunger driver 82. The plunger driver 82 can have a linear rack or plunger drive screw 84, plunger drive collar 86, and plunger drive plate 72. The ratchet handle 68 can be squeezed to rotate the plunger drive screw 84, as shown by arrow 87, or linear rack. The plunger drive screw 84 or linear rack can be configured to translate the plunger drive collar 86. For example, the plunger drive collar 86 can have internal threads engaging with outer threads of the plunger drive screw 84. The plunger drive collar 86 can be translatably fixed to the plunger drive plate 72. The plunger drive collar 86 and plunger drive plate 72 can translate distally with respect to the remainder of the syringe 74 when the ratchet handle 68 is squeezed. The plunger drive plate 72 can be in contact with and press the plunger 76 in a distal direction as shown by arrow.

The ratchet handle 68 can have a ratchet to prevent reversing the direction of the plunger driver, for example to prevent proximal translation of the plunger 76. A release lever can be rotated or deployed to release the ratchet mechanism for disengagement of the assembly, withdrawal of the system, or redeployment. The ratchet handle 68 can have no ratchet or a two-way ratchet, for example controlling the direction of the plunger driver 82, for example to allow proximal and distal translation of the plunger 76. The plunger drive plate 72 can be fixed to or touching but unfixed to the plunger 76.

Squeezing the ratchet handle 68 can depress the syringe plunger 94. Depressing the syringe plunger 94 can force inflation media from the syringe 74 to the media volume 12 of the dilation and/or everting catheter 18, for example pressurizing the respective balloons.

FIGS. 5A through 5F illustrates that the system handle 30 can have a stop cock and check valve 88 extending from the three-way connector 56. The stop cock and check valve 88 can be in fluid communication with the media volume 12. The stop cock and check valve 88 can be outside (as shown) or inside of the system handle case 34. The stop cock and check valve 88 can be accessed to add media, remove media, or check the pressure of the media in the media volume 12.

The system handle 30 can have one or more syringe detents 90. The syringe detents 90 can removably attach to a portion of the syringe 74 to prevent or minimize longitudinal translation of the syringe 74 with respect to the system handle case 34. The syringe detent 90 can be configured to allow the syringe 74 to slide in and out of the detent transverse to the longitudinal axis of the syringe 74.

The system handle case 34 can have a deflecting plate 92. The outer and/or inner catheters 4, 8 can press against the deflecting plate 92. The deflecting plate 92 can alter or deflect the path of the outer and inner catheters 4, 8 towards the longitudinally axial direction of the target site. The deflecting plate 92 can have a molded or formed groove, pins, plate, panel, or combinations thereof. The outer catheter 4 can be manufactured with a preset curve to accommodate the curved path within the system handle case 34.

The system handle case 34 can have a handle grip 96. The inner catheter 8 can have a linear inner catheter grip length 98. The inner catheter grip length 98 can be a length of the inner catheter 8 in the uneverted state in the handle grip 96. The inner catheter grip length 98 can be about 12 cm of inner catheter 8 in the uneverted state, for example corresponding to an eversion length for the inner catheter grip length 98 of about 6 cm (e.g., about 50% of the inner catheter grip length 98) of everted balloon membrane 24. Alternatively, the inner catheter 8 can be configured to coil up on wheel, have telescoping segments, or have folding and unfolding segments, to reduce the amount of distance needed within a system handle case 34 to accommodate the length of inner catheter 8 in the uneverted state.

The system handle 30 can have a reservoir-catheter channel 100, for example in fluid communication with the distal end of the syringe 74 and the proximal end of the inner catheter 8. The reservoir-catheter channel 100 can be a tube from the syringe connector 70 to the inner catheter 8.

The system handle 30 can have an access channel 102 extending from an external surface of the system handle connector 32 to an external surface of the system handle case 34. The access channel 102 can proximally terminate at a proximal access port 104.

The inner catheter 8 can extend through the access channel 102. One or more tools or fluids can be inserted through, and/or suction can be applied to, the proximal access port 104 and access channel 102 into and through or adjacent to the inner catheter 8.

The system handle 30 can have one or more drive gears 106. The drive gears 106 can be on one or opposite sides of the access channel 102. The drive gears 106 can encroach or impinge into the access channel 102. The drive gears 106 can be rotatably attached to the system handle case 34 via drive gear axles 108. The drive gears 106 can have teethed gear sections and drive gear grooves 124. The inner catheter 8 can extend through the drive gear grooves 124. The drive gears 106 can frictionally push and pull the inner catheter 8.

One or more of the drive gears 106 can extend and be exposed out of the system handle case 34. For example, the exposed drive gears 106 can be rotated by pressing on the exposed drive gear 106 with the user's palm or digit (e.g., thumb). The exposed drive gear 106 can be interdigitally engaged with one or more non-exposed drive gears 106. Rotating a first one of the drive gears 106 can rotate other drive gears 106 interdigitally engaged with the first drive gear 106.

The system handle case 34 can have a system handle case first lateral portion 110 and a system handle case second lateral portion 112. The system handle 30 can be made by attaching the system handle case first lateral portion 110 to the system handle case second lateral portion 112. Each drive gear axle 108 can be rotatably attached to the system handle case first lateral portion 110 and the system handle case second lateral portion 112.

The pump lever axle can be a ratchet handle axle 114. The ratchet handle 68 can rotate around the ratchet handle axle 114.

The system handle 30 can have a plunger drive rack 116. The plunger drive rack 116 can be fixed to the plunger drive plate 72. The plunger drive plate 72 can extend perpendicularly from the proximal end of the plunger drive rack 116. A side of the plunger drive rack 116 facing toward the plunger drive plate 72 can have unidirectional or bidirectional drive teeth 118.

The system handle 30 can have a ratchet handle spring 120 compressed between the system handle case 34, and/or the ratchet handle 68, and/or a ratchet arm 122. The ratchet handle spring 122 can reset the ratchet handle 68, for example by rotating the ratchet handle 68 forward, after the ratchet handle 68 has been squeezed.

The system handle 30 can have the ratchet arm 122 or actuating pawl. The ratchet arm 122 can be mechanically attached to the ratchet handle 68, for example to the handle spring 120. The ratchet arm 122 can be in a track limiting motion of the ratchet arm 122 to translation in the longitudinal direction with respect to the syringe 74. The proximal terminal end of the ratchet arm 122 can be curved in a u-shape. The terminal end of the ratchet arm 122 can press against a ratchet tooth. The ratchet arm 122 can be configured to pull the plunger drive rack 116 distally when the ratchet handle 68 is squeezed. The ratchet arm 122 is configured to move proximally with respect to the plunger drive rack 116 when the ratchet handle 68 is returned to a reset position.

The system handle 30 can have a locking pawl (not shown) can be spring-loaded between the system handle case 34 and the plunger drive rack 116, for example, allowing distal translation of the plunger drive rack 116 and preventing proximal translation of the plunger drive rack 116 except when the locking pawl is manually released from the plunger drive rack 116 by the release lever 126.

Figure 5A:
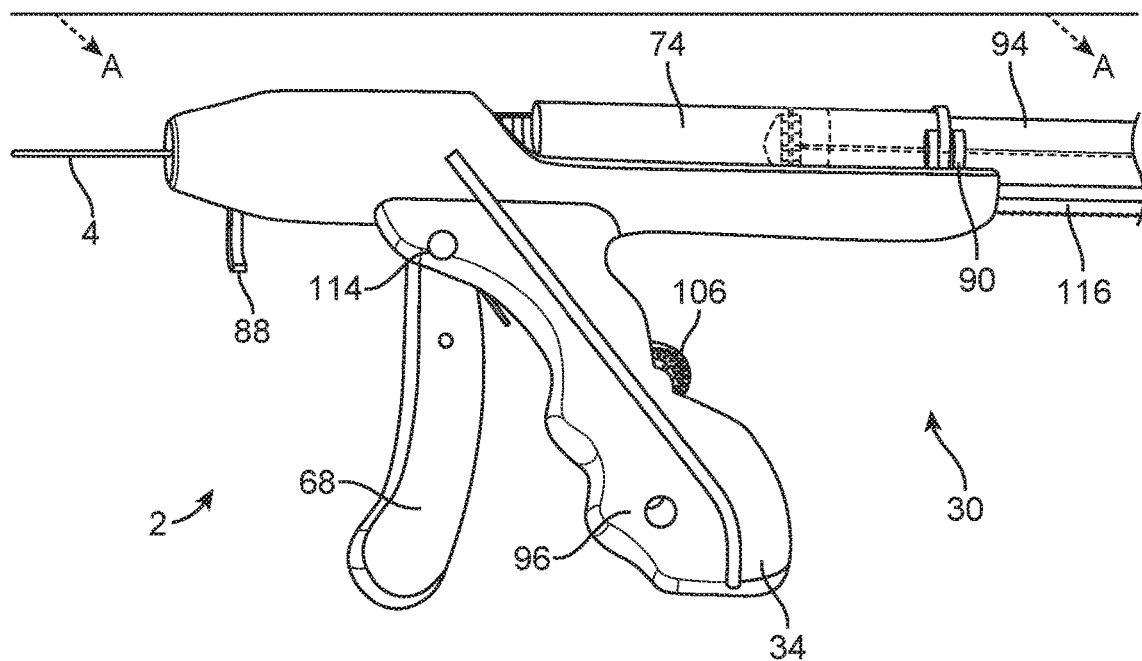
FIG. 5A illustrates a length of a variation of the everting balloon system.
Figure 5B:
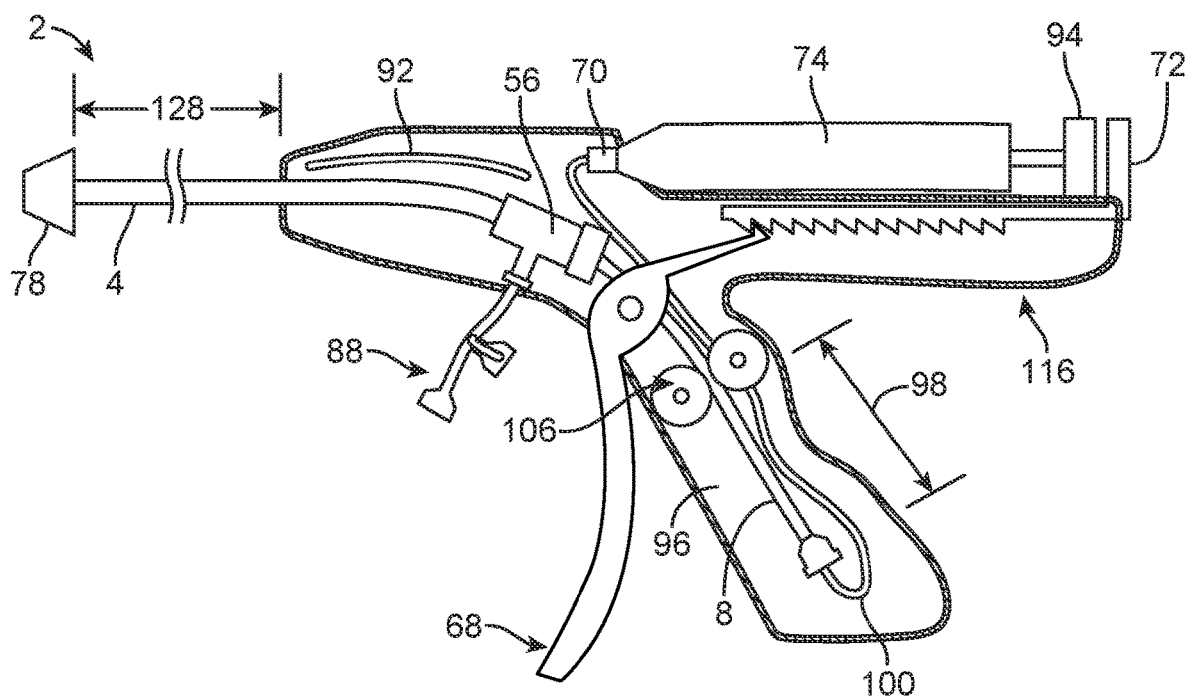
FIG. 5B is a partial cross-sectional view of a variation of the system of FIG. 5A.
Figure 5C:
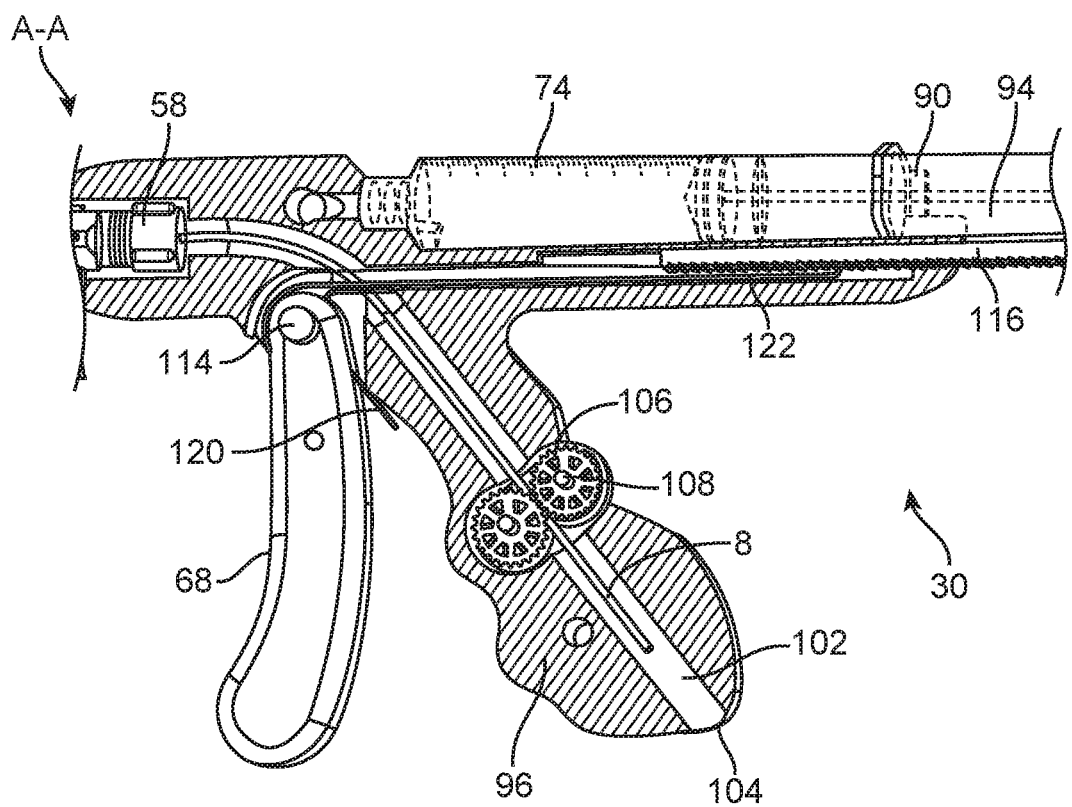
FIGS. 5C and 5D are variations of side and perspective views of a portion of cross-section A-A.
Figure 5D:
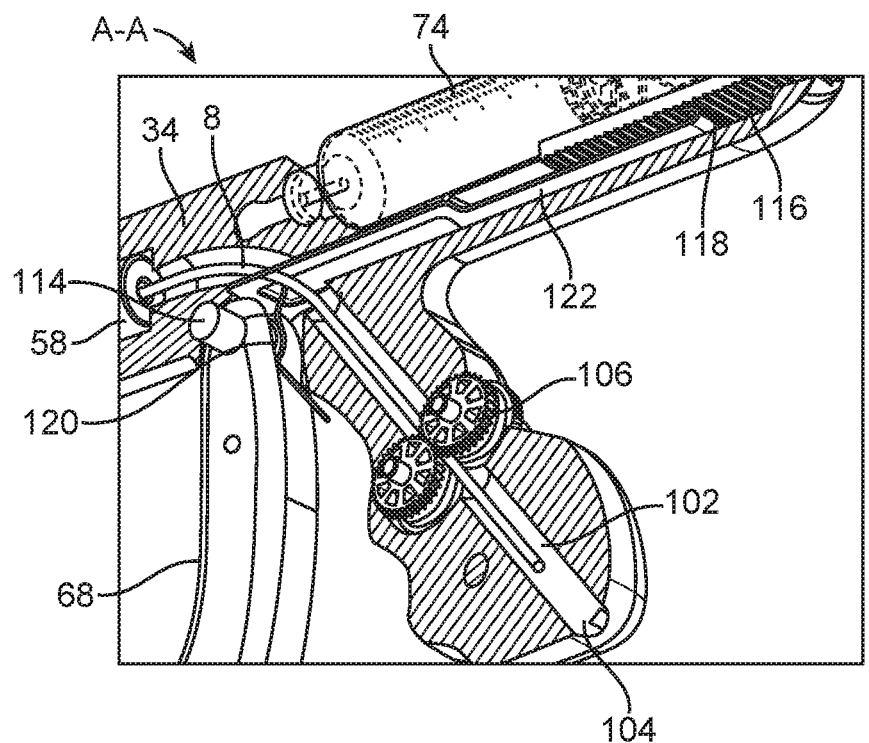
Figure 5E:
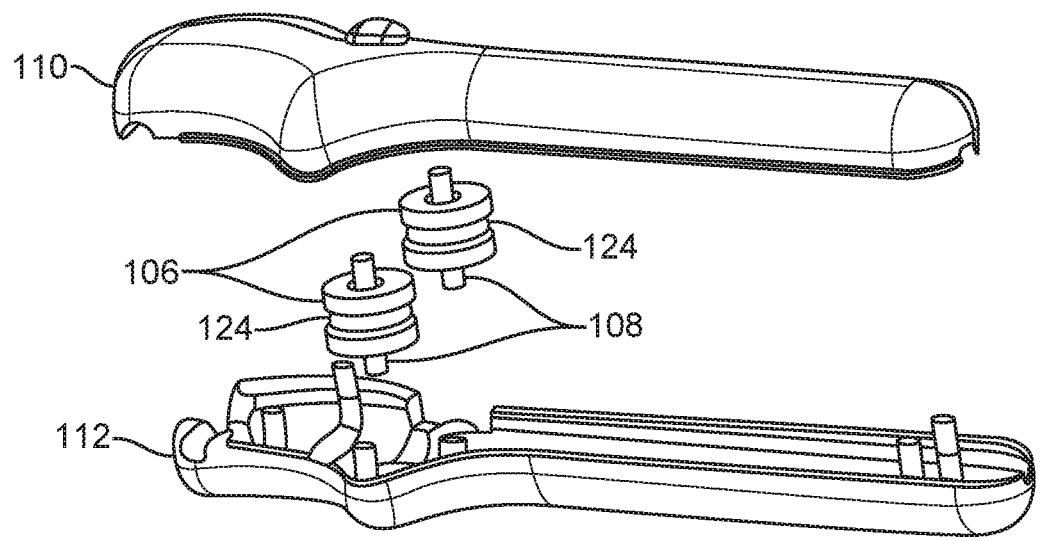
FIG. 5E is an exploded view of a variation of a portion of the system handle and the drive gears.
Figure 5F:
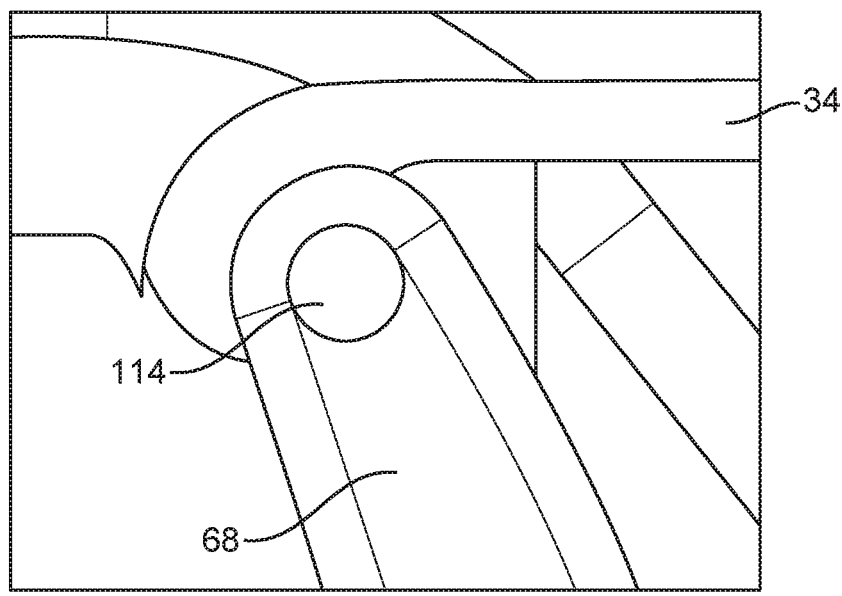
FIG. 5F is a close-up view of a variation of the system handle at the ratchet handle axle.

The outer catheter 4 can have an outer catheter length 128, as shown in FIG. 5B. The outer catheter length 128 can be from about 4 cm to about 35 cm, more narrowly from about 10 cm to about 24 cm, for example about 17 cm.

FIGS. 6A through 6D illustrate that the system handle 30 can have an inner catheter drive tray 130 translatably attached to the system handle case 34. A proximal length of the inner catheter 8 can extend proximally from the system handle case 34. The proximal length of the inner catheter 8 can be in, on, or adjacent to the inner catheter drive tray 130.

The syringe 74 can have a syringe loading connector 132, such as a luer connector, at the terminal distal or proximal end of the syringe 74 (e.g., the end further from the system handle case 34). A delivery tube 133 or delivery device can be attached to the syringe loading connector 132 and pressurized media can be delivered through the syringe loading connector 132 into the syringe 74.

Figure 6A:
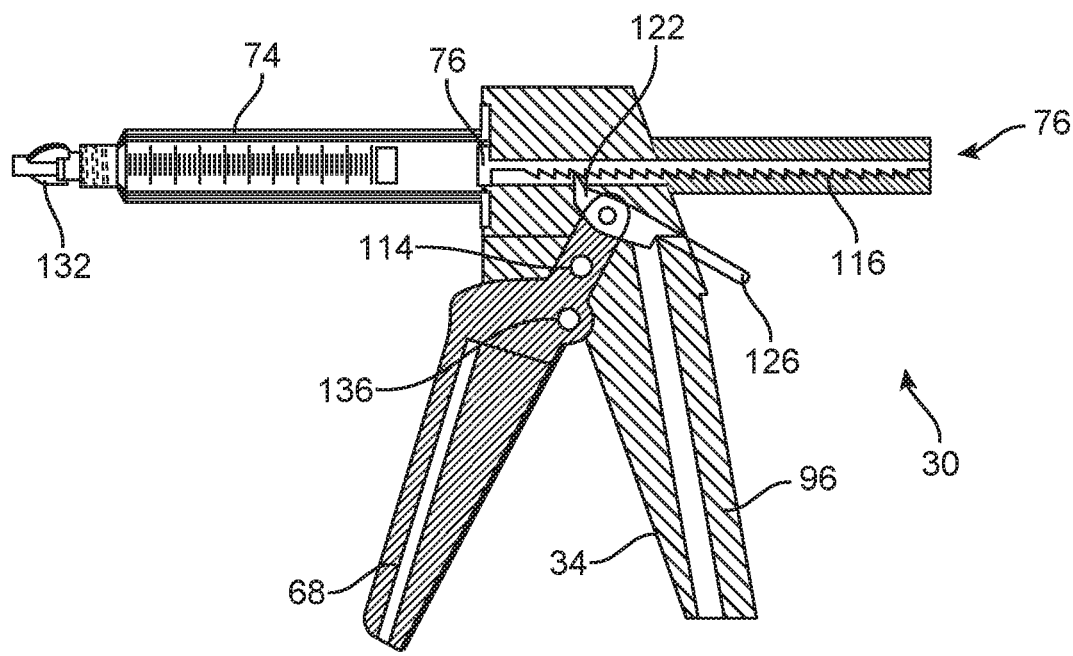
FIG. 6A is a cross-sectional view of a variation of the system handle.
Figure 6B:
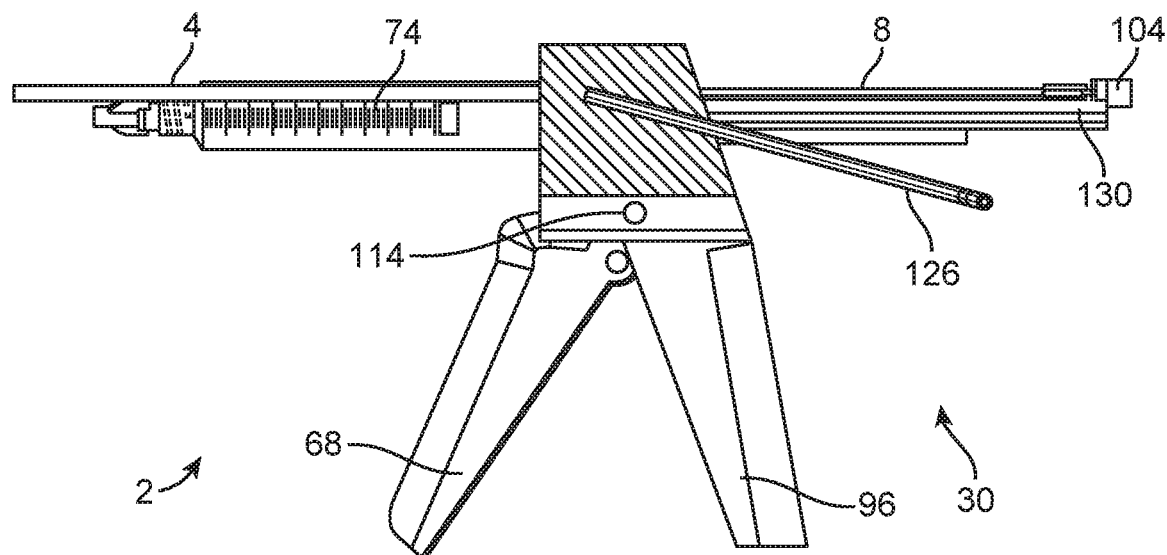
FIGS. 6B through 6D are side, top perspective and cross-sectional views, respectively, of a variation of the everting balloon system with the system handle of FIG. 6A.
Figure 6C:
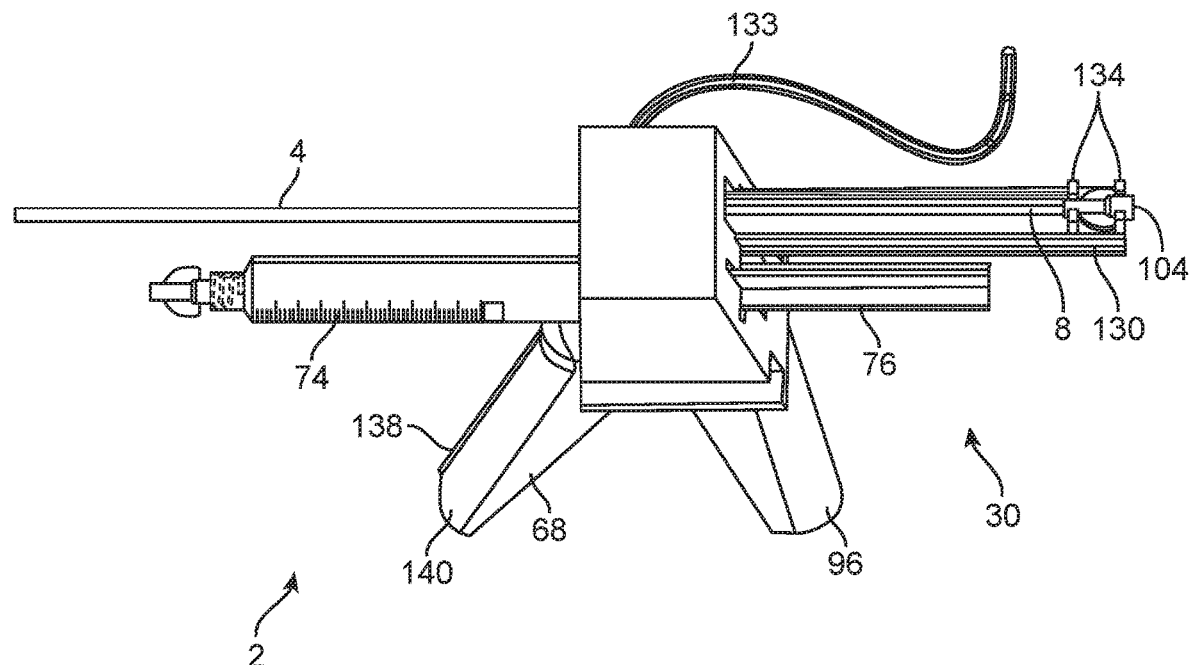

The delivery tube 133 or delivery device can be disconnected from the syringe loading connector 132 before deploying the everting balloon 18, as shown in FIG. 6C. The delivery tube 133 can wrap inside the handle grip 96 and connect the syringe 74 and its pressurization media to the three-way connector 56 and the hemostasis valve 58 or inlet port 40 for the dilation balloon 62.

The proximal terminal end of the inner catheter 8 can be attached to the proximal access port 104. The proximal end of the inner catheter drive tray 130 can have one or more access port detents 134. The access port detents 134 can attach to the proximal access port 104. The access port detents 134 can removably attach to a portion of the proximal access port 104 to prevent or minimize longitudinal translation of the proximal access port 104 with respect to the inner catheter drive tray 130. The access port detent 134 can be configured to allow the proximal access port 104 to slide in and out of the access port detents 134 transverse to the longitudinal axis of the inner catheter drive tray 130.

The inner catheter drive tray 130 can be translated along the longitudinal axis of the inner catheter drive tray 130 to translate the inner catheter 8 (e.g., advance the inner catheter 8 into the target site).

The system handle case 34 can have a fluid connection between the syringe 74 and the outer catheter 4, as disclosed herein.

Figure 6D:
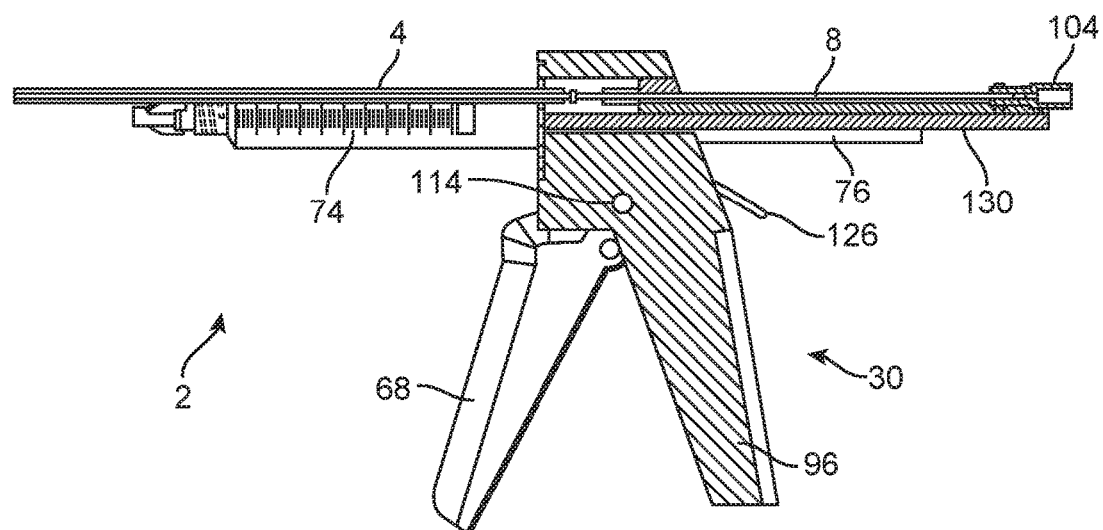

The ratchet arm 122 can extend away from the drive rack 116 to form a release lever 126, as shown in FIG. 6A. One or more other release levers 126 can extend from other locations on the system handle 30, as shown in FIGS. 6B and 6D. The release lever 126 can be rotated to disengage the ratchet arm 122 from the drive rack 116.

The ratchet handle 68 can have a safety lock hole 136. A safety lock having a cable or rod can removably extend through the safety lock hole 136, for example to create an interference fit against the system handle case 34 and prevent rotation of the ratchet handle 68, for example preventing unintentional or premature media delivery from the syringe 74.

The ratchet handle 68 can be laterally split into a catheter sub-handle 138 and a media sub-handle 140. The catheter sub-handle 138 can be configured to control the advancement of the inner catheter drive tray 130. The media sub-handle 140 can be configured to control the pressure of media delivery from the syringe 74. The catheter sub-handle 138 can be attached to an inner catheter drive rack. The media sub-handle can be attached to a plunger drive rack.

The ratchet handle 68 can control the syringe 74 for applying media pressure to the everting balloon 18 and dilating balloon 62, and independently control the translational movement of the inner catheter 8.

Figure 7A:
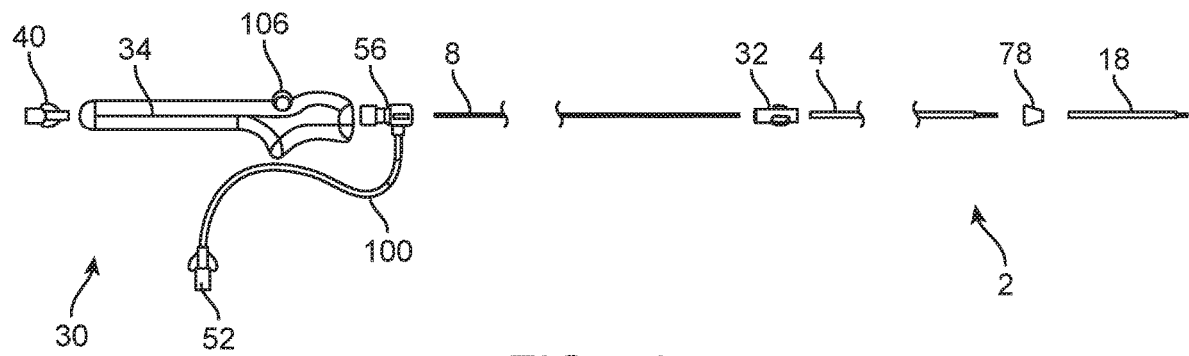
FIGS. 7A and 7B are exploded and perspective views, respectively, of a variation of the everting balloon system.
Figure 7B:
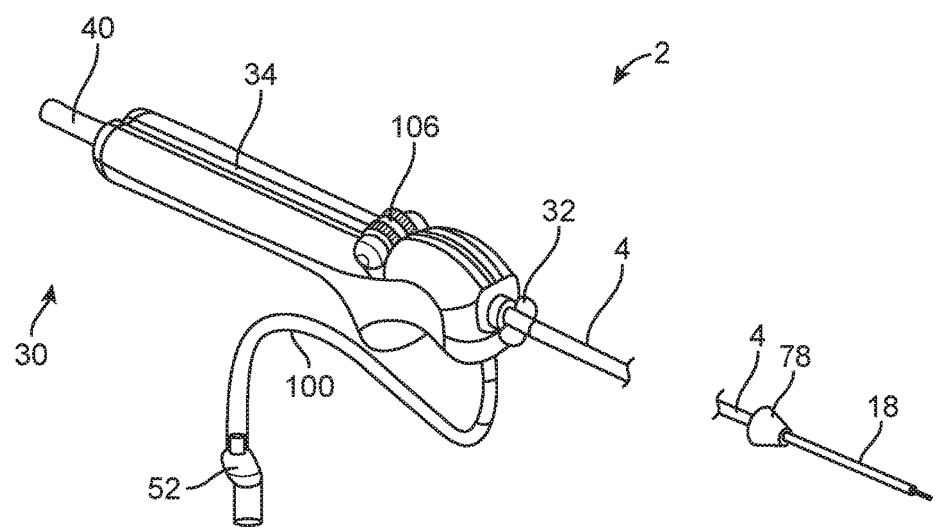

FIGS. 7A and 7B illustrate that the inlet port 40 can have a female luer connector. The system handle connector 32 can have a female luer connector. The outer catheter distal tip 78 can have a soft rubber or polymerized acorn tip, for example, to assist in stabilizing the everting system 2 at the opening of the bodily lumen or preventing unintentional advancement of the outer catheter 4 within the bodily lumen.

The reservoir-catheter channel 100 can extend from the three-way connector 56 and out of the system handle case 34. The proximal terminal end of the reservoir-catheter channel 100 can be attached to a female luer connector and/or the distal pressure valve 52. The distal pressure valve 52 and/or female luer connector can be connected to the liquid reservoir 42 (not shown).

Figure 8A:
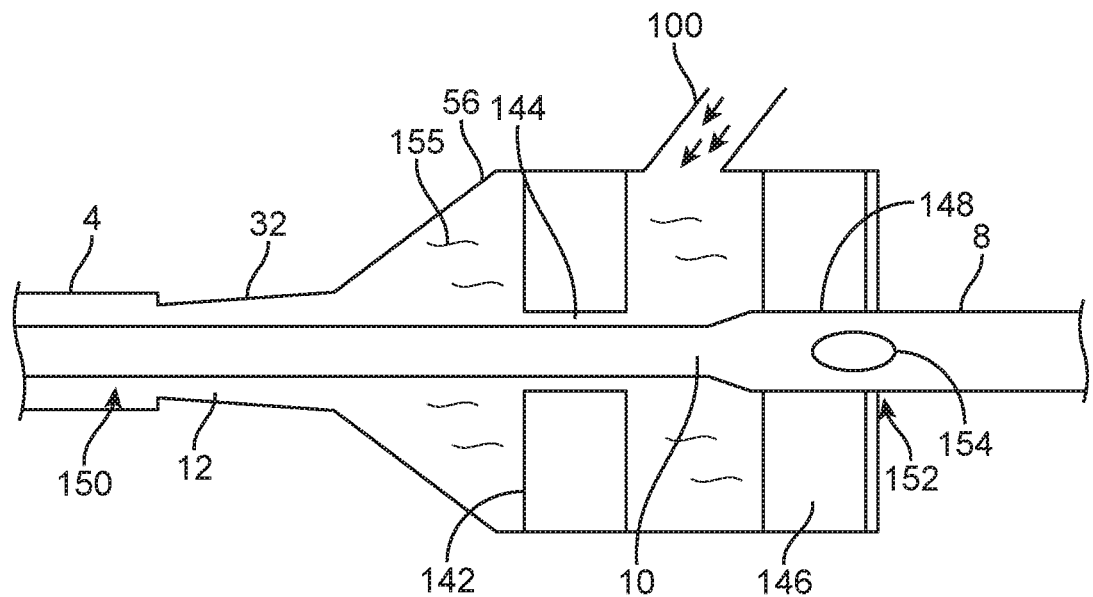
FIG. 8A is a cross-section view of a variation of the three-way connector and adjacent elements in a configuration to deliver media pressure to the outer catheter, for example to the everting balloon.

FIG. 8A illustrates that the three-way connector 56 can have a hemostasis valve 58. The three-way connector 56 can have or be a Touhy-Borst Y-connector. The inner catheter 8 can extend through the three-way connector 56.

The three-way connector 56 can have a distal gasket 142 between the reservoir-catheter channel 100 and the system handle connector 32. The distal gasket 142 can have a cylindrical distal gasket port 144 extending through the radial middle of the distal gasket 142. The distal gasket port 144 can have a distal gasket port diameter.

The three-way connector 56 can have a proximal gasket 146 proximal to the distal gasket 142. The proximal gasket 146 can be between the reservoir-catheter channel 100 and the proximal outlet through which the inner catheter 8 proximally exits the three-way connector 56. The proximal gasket 146 can be more, the same, or less compliant than the distal gasket 142. The proximal gasket 146 can have a cylindrical proximal gasket port 148 extending through the radial middle of the proximal gasket 146. The proximal gasket 146 can have a proximal gasket port diameter.

The inner catheter 8 can have an inner catheter small diameter length 150 and an inner catheter large diameter length 152 proximal to the inner catheter small diameter length 150. The inner catheter 8 can have an inner catheter proximal inflation hole 154 at the distal end of the inner catheter large diameter length 152. The inner catheter proximal inflation hole 154 can be in fluid communication with the open distal end of the inner catheter lumen 10 and/or the dilating balloon port 64.

Positive media pressure 14 or flow can be delivered, as shown by arrows, through the reservoir catheter channel 100 to the three-way connector 56. The inner catheter large diameter length 152 can occlude, plug, and/or seal the proximal gasket port 148. The positive media pressure 14 or flow can be delivered through the gap between the outer diameter of the inner catheter 8 (e.g., along the inner catheter small diameter length 150) and the inner diameter of the distal gasket port 144 and to the media volume 12 between the outer catheter 4 and the inner catheter 8, for example to the everting balloon 18.

Figure 8B:
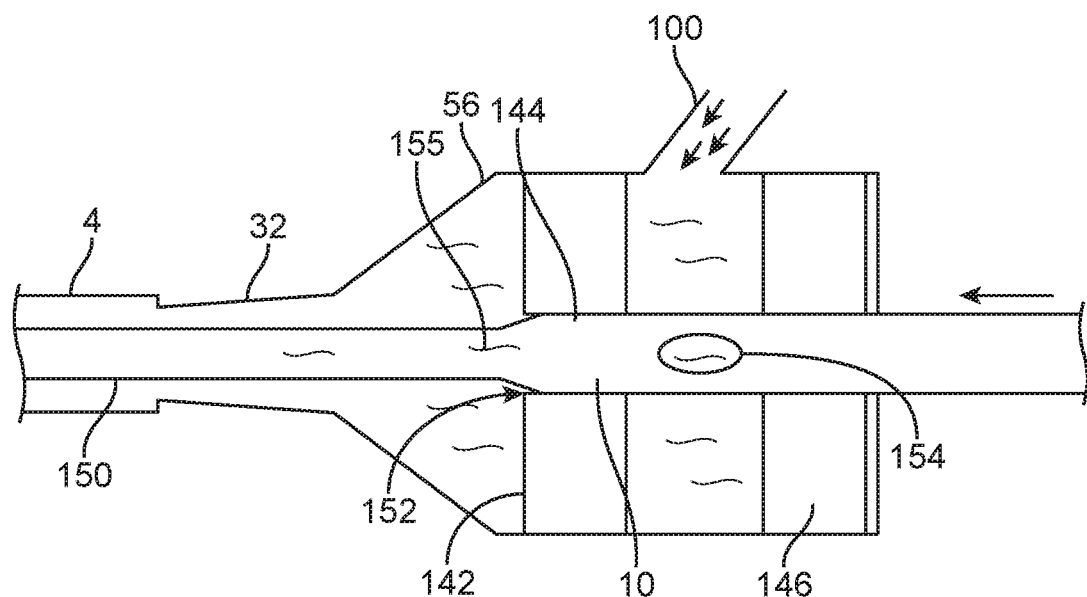
FIG. 8B is a cross-section view of a variation of the three-way connector and adjacent elements in a configuration to deliver media pressure to the inner catheter, for example to the dilating balloon.

FIG. 8B illustrates that the inner catheter 8 can be translated distally, as shown by arrow, at least until the inner catheter large diameter length 152 moves into the distal gasket port 144. The inner catheter large diameter length 152 can slide through the proximal gasket port 148. The inner catheter large diameter length 152 can occlude, plug, and/or seal the distal gasket port 144 and/or against the distal gasket 142. The media 155 flow from the reservoir-catheter channel 100 can be forced to flow into the inner catheter proximal inflation hole 154. The media 155 can flow down the inner catheter lumen 10, for example to the dilating balloon 62.

An exemplary procedure for dilating the a body lumen such as the cervical canal can include:
1. The syringe 74 can be loaded onto the system handle 30. The system handle 30 can be a separate, reusable item in which the everting catheter and syringe filled with media 155 can be attached to the remainder of the system before use. Alternatively, the system handle 30 can come supplied to the end user preassembled with the remainder of the system and pre-filled, or combinations thereof.
2. The distal end of the everting balloon system 2 can be placed at the exocervix.
3. The ratchet handle 68 can be depressed. The first one to two clicks of the ratchet (i.e., as the locking pawl passes over ratchet teeth) can depress the syringe plunger 94 and pressurize the everting balloon 18. The everting balloon 18 can be pressurized to 4 to 6 atmospheres.
4. The ratchet handle 68 can be depressed further (or released to rotationally reset and then depressed further). The next sets of clicks on the ratchet handle 68 can indicate advancement the inner catheter 8. This can be accomplished by the ratchet mechanism rotating gear wheels on the inner catheter 8 and/or translating a linear rack to advance the inner catheter 8.
5. The ratchet handle can be depressed further (or released to rotationally reset and then depressed further). The advancement of the inner catheter 8 can continue until the everting balloon is fully deployed and everted. The dilation balloon 62 can be positioned on the distal end of the inner catheter 8.
6. The ratchet handle 68 can be depressed further. The next click of the ratchet can de-pressurize the everting balloon 18.
7. The ratchet handle 68 can be depressed further. The next click of the ratchet can change the pressurization outlet of the syringe 74 from the everting balloon 18 to the dilation balloon 62. This can be accomplished, for example, by:
   a. rotating a valve with the ratchet mechanism,
   b. manually rotating the valve, and/or
   c. advancing the inner catheter 8 to where the inner catheter proximal inflation hole 154 or port is exposed to the inflation media, such as shown in FIGS. 8A and 8B.
8. The ratchet handle 68 can be depressed further. The next sets of clicks on the ratchet can indicate the inflation of the dilatation balloon 62.
9. The dilatation balloon 62 may rupture the overlying everting balloon 18.
10. The amount of force in the biological lumen dilatation can be governed by a pressure relief valve or by the amount of volume of media 155 that can be placed within the dilatation balloon 62. The dilatation pressure can be monitored by a pressure gauge in or attached to the system handle case 34. The dilation balloon 62 can dilate the cervix with from about 6 atmospheres to about 20 atmospheres. The dilation balloon 62 can initially deliver about 10 atmospheres to about 12 atmospheres with a reduction in pressure as the cervix dilates and the dilatation process is completed. The system can deliver a known volume of media 155 into the dilation balloon 62 irrespective of quantifying or measuring the media pressure 14.
11. The dilatation process may be observed by ultrasound or radiographic imaging.
12. A pressure relief button on the system handle 30 can be activated to remove or reduce dilatation pressure in the media volume 12 in the inner catheter lumen 10.
13. The syringe plunger 94 may be retracted to draw vacuum from the inner catheter lumen 10 and dilation balloon 62, for example loosening the dilation balloon 62 from the cervix, and/or deflating the dilation balloon 62, for example to facilitate removal of the everting balloon system 2 from the cervix.
14. The everting balloon system 2 can be re-pressurized, for example if additional dilatation force is desired in the cervix. For instance, if an additional stenosis in the cervix is visible, the dilatation balloon 62 can be repositioned and inflated in the additional stenosis area.

The everting catheter system can access a bodily cavity (e.g., the uterine cavity or fallopian tubes) to deliver or introduce of tools (e.g., instruments), reproductive (e.g., embryos, in vitro fertilization (IVF) or insemination products, such as hormones) media 155 or material, contrast media, dye, therapeutic agents, sclerosing agents to treat the endometrium, insufflation media, or combinations thereof to the cavity. For example, reproductive media can be delivered with a transfer catheter inserted through the inner catheter lumen 10 to the uterine cavity.

Figure 9:
FIG. 9 is an exploded view of a variation of a transfer catheter.

FIG. 9 illustrates that a transfer catheter 156 or insemination catheter can have a transfer connector 158, such as a female luer connector, a strain relief length 160, and a transfer tube 162. The transfer tube 162 can hold the reproductive media. The transfer tube 162 can have a proximal length having a proximal length diameter larger than a distal length diameter of a distal length of the transfer tube 162. A delivery force, for example a positive fluid pressure, can be delivered through the transfer connector 158 and strain relief length 160 to push the contents of the transfer tube 162 into the target site.

The transfer catheter 156 can attach to or inserted through the inlet port 40. The transfer tube 162 can hold an embryo, for example for in vitro fertilization or IVF. The embryo transfer catheter 156 can deliver embryos through the system and to the uterine cavity. The transfer catheter 156 can hold spermatozoa and through the system and to the uterine cavity for intrauterine insemination procedures. The transfer catheter 156 can hold and deliver other materials the deposition of drugs, therapeutic agents, instruments, endoscopes, cytology brushes, other catheters, or combinations thereof through the system and into the uterine cavity. The transfer catheter 156 can be connected to a vacuum source for the aspiration of materials from the uterine cavity or other bodily cavities and lumens.

The transfer catheter 156 and/or materials can be loaded in the inner catheter lumen 10 prior to everting the everting balloon 18 within the vessel or bodily cavity. For example in the case of delivery of reproductive material in the uterine cavity, the transfer catheter 156 can be loaded with washed and prepared semen in the transfer tube 162 and the transfer catheter 156 can be placed in the inner catheter lumen 10.

A guidewire can be inserted through the transfer catheter 156 and/or the remainder of the system, for example to direct the tube or system to the target site 164. The guidewire can be used for recanalization.

The inner catheter 8 can be extended and the everting balloon 18 can evert and unroll through the cervix and into the uterine cavity. Concurrently or subsequently, the transfer catheter 156 can be advanced through the inner catheter lumen 10 into the uterine cavity. Once fully everted or when the transfer catheter 156 becomes extended or exposed from the inner catheter 8 and beyond the everting balloon membrane 24, the reproductive material 166 in the transfer catheter 156 can be deposited by a syringe 74, squeeze bulb, piston, or other pressure system. A second delivery catheter, such as a second insemination, IVF, or drug delivery catheter can be concurrently inserted into the inlet port 40 or a second inlet port. The second delivery catheter can be deployed to the target site 164 concurrent with or subsequent to the transfer catheter 156.

The system handle 30 can have a lead-in area. The lead-in area can, for example, be without steps, edges, bumps, or restrictions that may impede or contact the distal opening of the transfer catheter 156 during passage, for example so that in the case of delivery of insemination material, the transfer catheter 156 can be easily loaded into the system handle 30.

An insemination syringe 74 or pump can be attached to the proximal transfer connector to deliver pressure to the transfer tube 162, for example to expel the reproductive material 166 once the distal port of the transfer catheter 156 is positioned at the target site 164 (e.g., after the everting balloon 18 is fully deployed). The actuation of the insemination syringe or pump on a pre-loaded transfer catheter 156 can be performed by the same hand that holds and operates the components of the everting catheter system.

In addition, the transfer catheter 156 can be configured to be introduced into the proximal connector in the handle of the everting catheter system once the system is fully deployed.

The user can perform any or all of the following while using the everting balloon system 2, for example with a single hand:
a. pressurize the everting catheter system;
b. position the everting balloon system 2 at the patient's cervix;
c. maintain the everting balloon system 2 position throughout the procedure;
d. advance the inner catheter 8 and everting balloon 18;
e. once extended beyond the everting balloon membrane 24 or inner catheter 8, present the transfer catheter 156 for deposition into the bodily cavity such as a uterine cavity
f. retract the inner catheter 8 and everting balloon 18; and/or
g. activate (e.g., toggle) the pressure release lever to remove or release hydraulic or pneumatic pressure from the media volume 12.

Figure 10A:
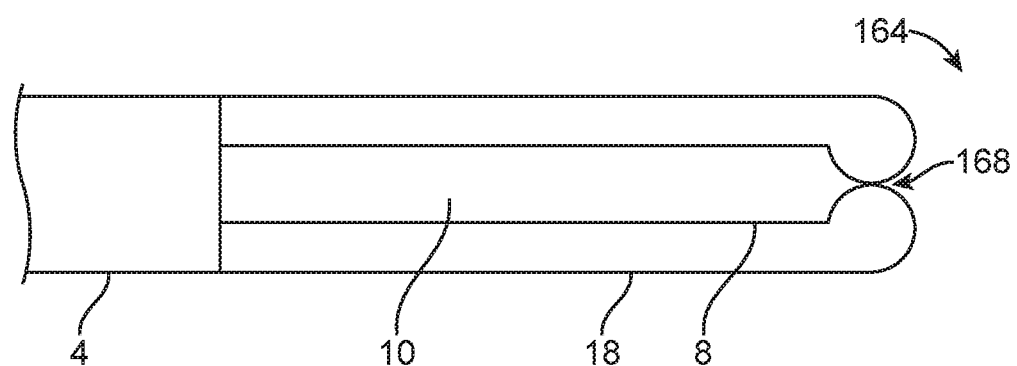
FIGS. 10A through 10C illustrate a variation of method for delivering material to a target site, such as reproductive material delivered to a uterine cavity.
Figure 10B:
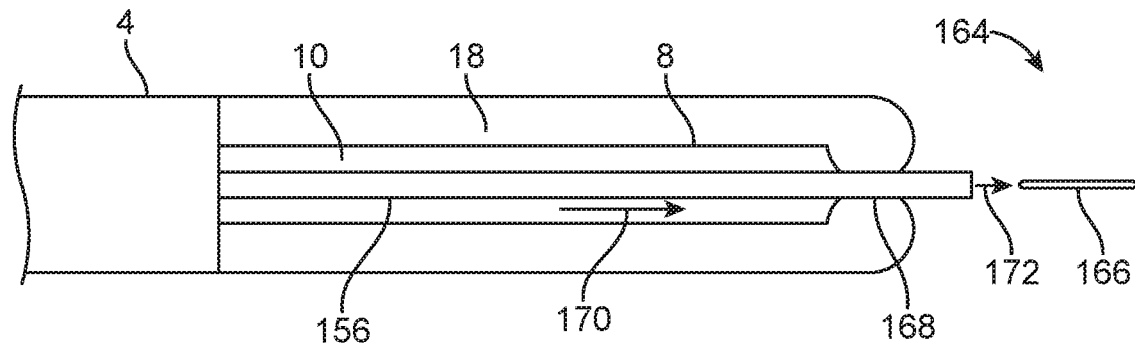
Figure 10C:
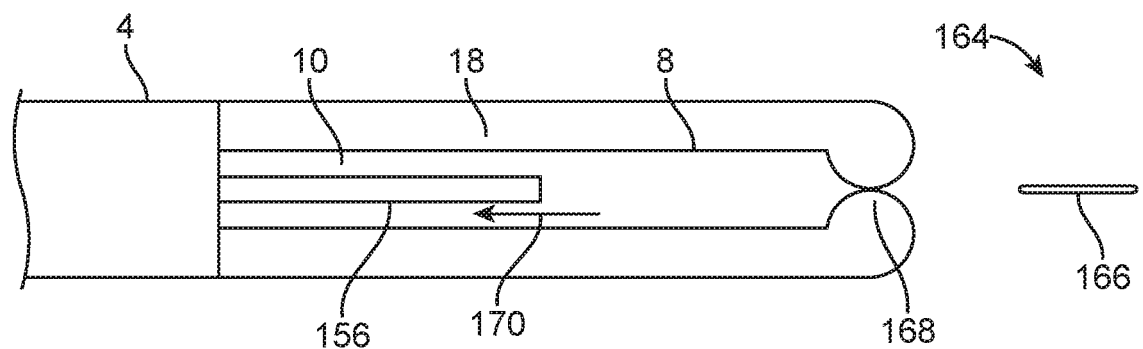

FIGS. 10A through 10C illustrate that the distal end of the everting balloon can form a balloon check valve 168. The length of the everting balloon 18 distal to the distal terminal end of the inner catheter 8 can radially contract to form a tight orifice that can be the balloon check valve 168. The balloon check valve 168 can be an openable barrier that can block or interrupt fluid communication between the inner catheter lumen 10 and the target site 164.

The balloon membrane 6 can have from about 1 mm to about 3 mm of overlapping wall at the balloon check valve 168 closing off the inner catheter lumen 10. The strength or closing pressure of the balloon check valve 168 can be modulated during use. For example the distance of overlap of balloon membrane 6 can be increased or decreased by controlling the amount of excursion available for the inner catheter 8 and everting balloon membrane 24.

FIG. 10B illustrates that the distal end of the transfer catheter 156 can be advanced, as shown by arrow 170, through the inner catheter lumen 10, through the balloon check valve 168, and to the target site 164. The transfer catheter 156 can penetrate or push open the balloon check valve 168 when the transfer catheter 156 moves through the balloon check valve 168. When the terminal distal end of the transfer catheter 156 is distal of the balloon check valve 168 and at the target site 164, the reproductive material 166 loaded in the transfer catheter 156 can be delivered 172 through a distal port of the transfer catheter 156 and into the target site 164, such as the uterine cavity.

FIG. 10C illustrates that the transfer catheter 156 can be retracted through the balloon check valve 168 and the inner catheter lumen 10 after the reproductive material is deposited at the target site 164. The balloon check valve 168 can close as the transfer catheter 156 is retracted through the balloon check valve 168. The balloon check valve 168 can maintain a seal between the inner catheter lumen 10 and the target site 164 when the transfer catheter advances 170 through, remains stationary within, and is retracted through the balloon check valve 168.

The reproductive material 166 can be isolated from vacuum effect or the retraction of reproductive material 166 from the target site 164 as a result of the vacuum forces created by the withdrawal of the transfer catheter 156 through the system once the deposition of reproductive material 166 is completed. The balloon check valve 168 can reduce or eliminate vacuum effect for embryo transfer.

The balloon check valve 166 can be a tactile indicator for the physician when passing the transfer catheter 156 through the everting balloon system 2. In transfer procedures, depending upon physician preference or patient anatomy, for example, the amount of insertion of the transfer catheter 156 through the distal end of the everting system can vary from patient to patient. As the distal end of the transfer catheter 156 passes through the balloon check valve 168, the resistance created by the balloon check valve 168 can be felt by the physician on the proximal end of the transfer catheter 156. Depending upon the length of balloon chosen to act as a balloon check valve 168, the degree or amount of resistance can be modulated. In some procedural settings there may be a compromised ability to see the amount of insertion of the transfer catheter 156 into the everting balloon 18, or physical depth indicia or markings on the proximal end of the transfer catheter 156. The compromised ability to see may be due to low light within the procedure room so that imaging and visualization of monitors can be enhanced. In addition, the physical relationship of the physician, embryologist, or other persons or equipment in the procedure room may compromise the ability to see easily the amount of insertion into the everting catheter. The tactile sensation of the resistance of the balloon check valve 168 can create a palpable indicator that the transfer catheter 156 is at the distal end of the everting balloon 18.

The everting balloon system 2 can be used to access and seal the uterine cavity, for example, for the deposition of reproductive material 172 for long duration intrauterine insemination.

Figure 11A:
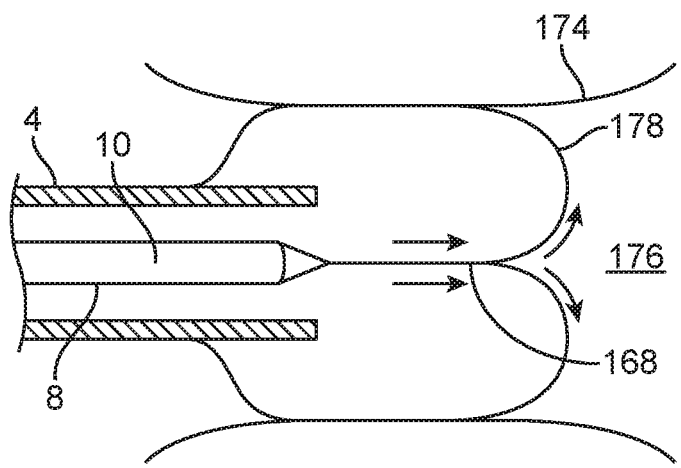
FIGS. 11A through 11C illustrate a variation of a method for delivering material to a target site, such as reproductive material delivered to a uterine cavity.
Figure 11B:
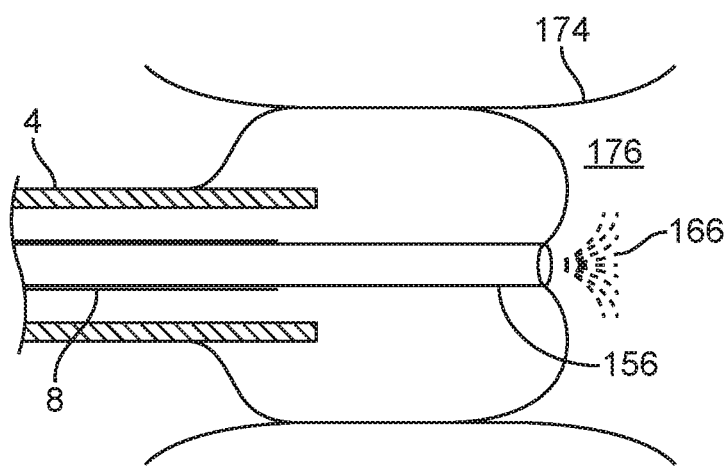
Figure 11C:
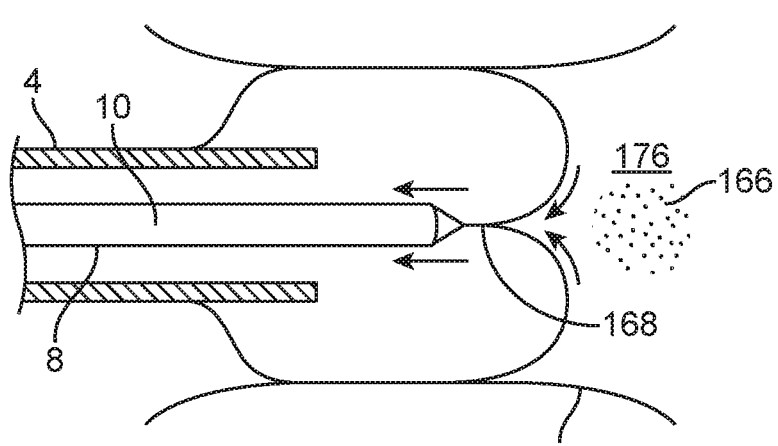

FIGS. 11A through 11C illustrate that the everting balloon membrane 24 can create a seal within the cervical canal (e.g., against the cervical canal walls 174) as the everting balloon 18 traverses the cervical canal. FIG. 11A illustrates that the everting balloon membrane 24 can unroll and advance along the cervical walls, as shown by arrows, as the balloon is pressurized and the inner catheter 8 is distally advanced. The outer catheter 4 can also seal against the cervical canal wall 174. For example, the outer catheter 4 outer diameter can be equal to the everting balloon outer diameter.

FIG. 11B illustrates that the transfer catheter 156 can advance distally within the everting balloon 18 and the inner catheter lumen 10. The transfer catheter 156 can deposit the reproductive material 166 (e.g., sperm) within the uterine cavity 176.

FIG. 11C illustrates that the transfer catheter 156 and/or the inner catheter 8 can be retracted (e.g., from about 3 mm to about 10 mm) or inverted, as shown by arrows, to close the distal end of the inner catheter lumen 10, as shown by arrows, with respect to the uterine cavity 176. The distal opening of the balloon 178 can close, for example due to the pressure within the everting balloon 18 forcing the everting balloon 18 to form the balloon check valve 168. The balloon check valve 168 can seal the cervical canal and the uterine cavity 176 from the inner catheter lumen 10. The reproductive materials 166 can remain in the uterine cavity 176 without being expelled through the cervix.

FIG. 12 illustrates that the outer catheter 4 and inner catheter 8 can be configured to be de-coupled from the everting balloon membrane 24 and a distal closure tip 180. The distal closure tip 180 can be configured to connect to and seal off the everting balloon 18.

After delivery of the reproductive materials 166 to the uterine cavity 176 (i.e., insemination) is complete, the outer and inner catheters 4, 8 can be decoupled from the everting balloon 18 and the distal closure tip 180. After the catheters are removed from the everting balloon 18, the everting balloon 18 can remain inflated or pressurized. A one-way balloon closure check valve that can remain within the distal closure tip 180 when the catheters are removed. The one-way balloon closure check valve can be connected to the balloon membrane 6 with a conduit within the distal closure tip 180 and can seal the everting balloon 18. A one-way check valve such as a duck bill valve within the distal closure tip 180 can keep the reproductive material 166 in the uterine cavity.

After the outer catheter 4 and inner catheter 6 are de-coupled from the balloon 178 and removed from the cervix, the distal closure tip 180 can remain in the cervical canal and/or the vagina. The distal closure tip 180 can be made from biocompatible materials and a low durometer, soft and conformable silicone. The everting balloon 18 can remain pressurized and sealing the cervical canal.

The distal closure tip 180 can have a plug 182 sealing the balloon 178 and a pull string 184 attached to the plug 182. (The pull string 184 can be made from materials known for use for strings used commonly in tampons.) After a desired duration of time of keeping the cervical canal sealed without allowing the reproductive material 166 (e.g., sperm) to exit the uterine cavity 176, and reproductive tract of the female, through the cervix, the everting balloon 18 can be deflated and/or removed by pulling on the pull string 184 to remove the plug 182, or pulling directly on the plug 182. The pull string 184 can be connected to the plug 182. The plug 182 can be connected to a proximal port of a pressurization release channel 186 in fluid communication with the everting balloon 18. For example, the pull string 184 is connected to the plug 182 and the length string can continue further by being connected to the distal closure tip 180. Before, during, or after the everting balloon 18 is deflated, the remaining elements can be removed from the cervix. The distal closure tip 180 may or may not be removed until after the everting balloon membrane 24 is deflated.

The pull string 184 can be pulled by the physician or healthcare professional or alternatively, by the patient at home. The patient can be ambulatory while the everting balloon 18 remains in the cervical canal. While sealed, the reproductive material 166 can be contained within the uterine cavity 176 without being expelled through the cervix by gravity, contractions, or movements by the patient.

The distal closure tip 180 can have a pressurization release channel 186 in fluid communication with the everting balloon 18 and a pressurization release check valve 188. The pressurization release check valve 188 can be a one-way check valve. The pressurization release check valve 188 can be opened to depressurize and deflate the everting balloon 18. The deflated balloon 178 can then be removed from the cervical channel by the patient or physician. For instance, the pressurization release check valve 188 can have a duck bill valve that can allow air and fluid to travel into the distal tip and pressurize the everting balloon membrane 24. The everting balloon 18 can be inflated or the internal pressure can be increased through the pressurization release check valve 188.

The pressurization release check valve 188 can be attached to a pull string 184. For example, the pull string 184 can be attached to the body of the duck bill valve. The user can pull the pull string 184, removing the duck bill valve from the distal closure tip 180, deflating the everting balloon 18, and then removing the distal closure tip 180 and everting balloon 18.

Figure 12A:
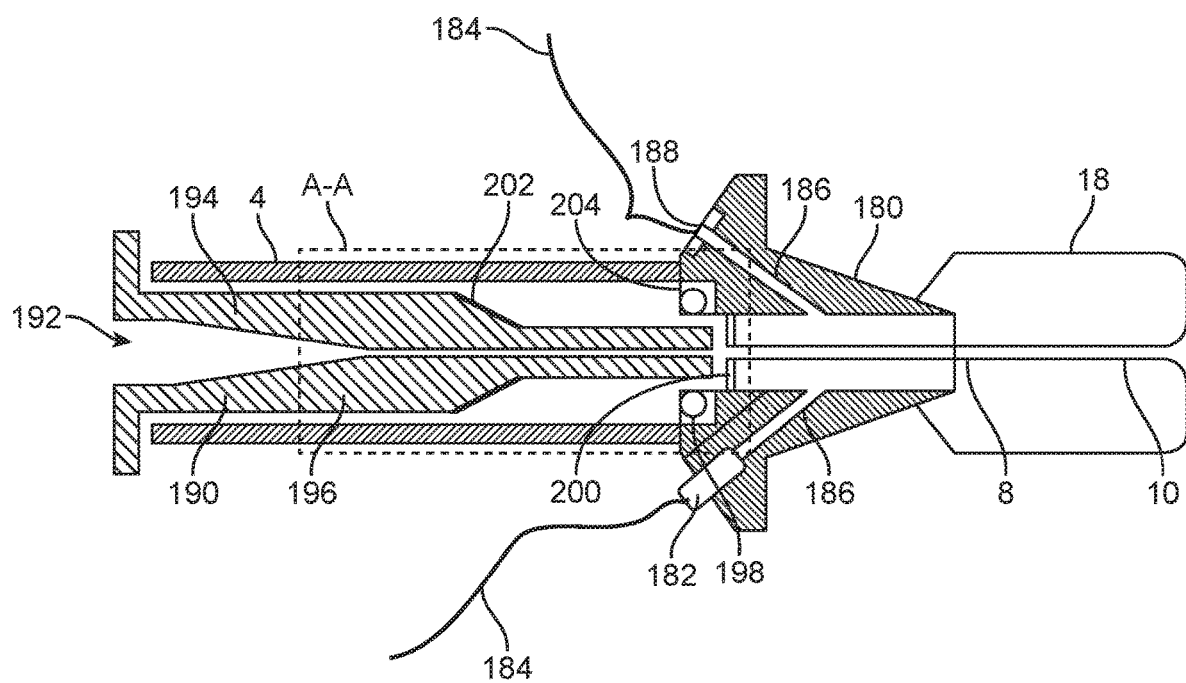
FIG. 12A is a longitudinal cross-sectional view of a variation of the distal end of the everting balloon system.

FIGS. 12A, B, and C illustrate that the system can have an inner catheter plunger 190 in the outer catheter. The proximal terminal end of the inner catheter plunger 190 can have a plunger proximal connector 192. The plunger proximal connector 192 can have a port or hole, for example configured to connect to a fluid delivery device to fill the everting balloon 18 and/or plunger 76 housing with pressurized media 155 (e.g., saline, air). The everting balloon 18 can also be pre-filled with media 155 and fluidly sealed.

The inner catheter plunger 190 can have a plunger first body 194 and a plunger second body 196. The distal closure tip 180 can have a plunger o-ring 198 configured to form a seal around the inner catheter plunger 190 where the inner catheter plunger 190 enters the distal closure tip 180. The terminal proximal end of the inner catheter 8 can be attached to inner catheter stop 200. The inner catheter stop 200 can have a sealing gasket (e.g., the plunger o-ring 198 and/or a different sealing element) exterior to and concentric with the inner catheter 8.

The diameter of the inner catheter plunger 190 can decrease at a discreet slope along the length of the inner catheter plunger 190. The radially outer side of the distal end of the inner catheter plunger 190 can have one or more mechanical decoupling detents 202, for example, on the discreet slope. The decoupling detents 202 can extend radially beyond the radially outer surface of the remainder of the distal end of the inner catheter plunger 190.

The terminal proximal end of the distal closure tip 180 can have one or more coupling connectors 204. The coupling connectors 204 can have one or more flanges configured to releasably attach to the distal terminal end of the outer catheter 4.

The inner catheter plunger 190 can be configured to distally advance the inner catheter 8. The inner catheter plunger 190 can press against the inner catheter stop 200, translating and everting the inner catheter 8. After being fully distally advanced to a fully everted position, the inner catheter 8 can be exposed to the target site 164 and ready for the delivery of reproductive material 166 to the target site 164. After delivery of the reproductive material 166 to the target site 164, the inner catheter 8 can be retracted, for example by retracting the inner catheter plunger 190, until a mechanical stop is reached and the plunger 76, plunger proximal connector 192, and outer catheter 4 become disconnected from the inner catheter 8 which remains within the distal closure tip 180. The sealing gasket can be on the exterior circumference of the inner catheter 8, for example, to prevent leaking of, and keep pressurization of the everting balloon 18 pressurized. The outer catheter 4, containing the proximal connector 206 and plunger 76, can be disconnected from a coupling with the distal closure tip 180 by a number of possible manipulations including twisting, pulling, or pressing an actuator, or combinations thereof. The decoupling can be automatic when the distal end of the proximal connector 206 mechanically engages and expands the flanges to release the coupling on the outer catheter 4.

Figure 12B:
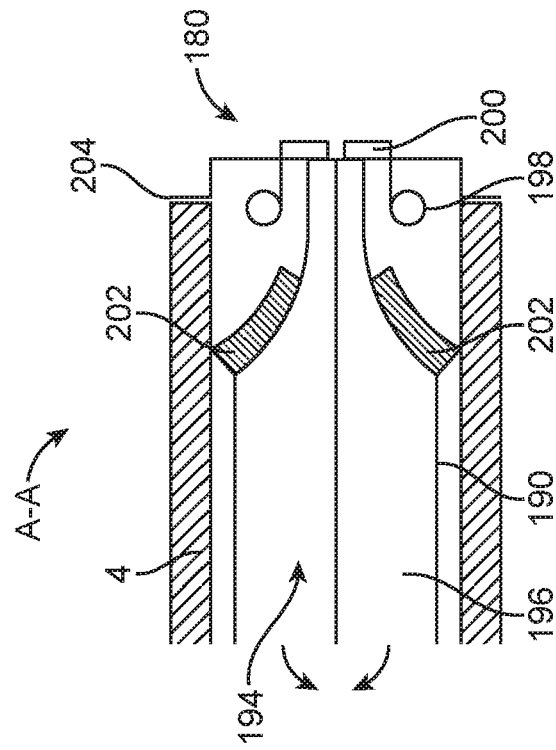
FIGS. 12B and 12C are close-up section A-A of the system of FIG. 12A with the outer catheter in configurations attached to the distal closure tip and detached from the distal closure tip, respectively.

FIGS. 12B illustrates that the inner catheter plunger can be in an attached configuration, not exerting radially outward pressure on the outer catheter.

Figure 12C:
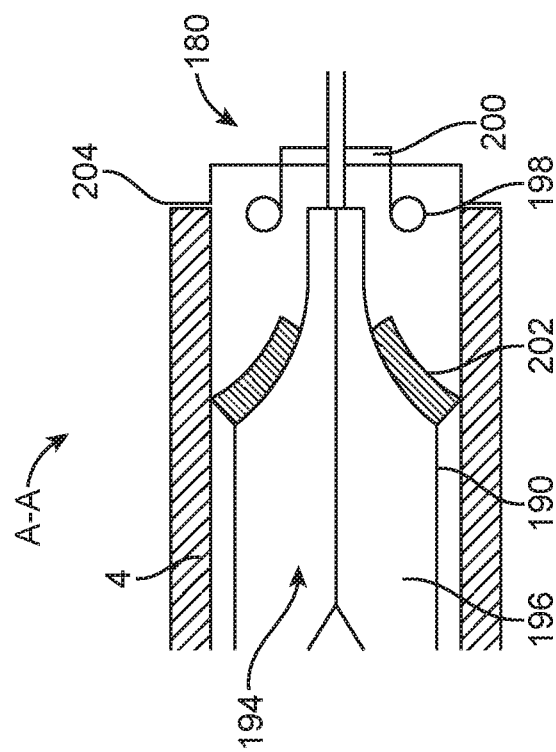

FIG. 12C illustrates that the proximal ends of the plunger first body 194 and plunger second body 196 can be rotated toward each other, as shown by arrows, causing a radially outward rotation of the distal ends of the plunger first 194 and second bodies 196. The detents can press the outer catheter 4 radially outward. The radial expansion of the outer catheter 4 can expand the distal terminal end of the outer catheter 4. The outer catheter 4 can then disengage from the coupling connector 204 and the distal closure tip 180. The subsequent withdrawal of the outer catheter 4 can remove the distal end of the proximal connector 206 from the inner catheter 8. The inner catheter 8 can remain in the distal closure tip 180.

After full deployment of the everting balloon membrane 24 and deposition of reproductive material 166, the motion of the proximal connector 206 in the proximal or retraction (e.g., reverse) direction to create a one-way balloon check valve can mechanically disengage the coupling connector 204 (e.g., flanges) by use of ramps, detents, bumps, or steps that mechanically act on the flange, or the outer catheter housing itself, to then decouple the outer catheter 4, proximal connector 206 and plunger 76 from the distal closure tip 180.

The everting balloon 18 can be pressurized through the pressurization release check valve 188 within the distal closure tip 180 and maintained by a plug 182 with pull string 184 attached. For example, the plug 182 can be inserted into the pressurization release check valve 188. Any of the liquid reservoirs 42 and respective pressurization systems can be used, such as a syringe 74, inflation device, and/or air or fluid pump.

The pressurization release check valve 188 and the plug 182 can be within the same component. For example, a releasable one-way valve such as a duckbill valve can be attached to a pull string 184. The pressurization release check valve 188 and/or plug 182 can be dislodged from the respective sealing areas, for example, providing reinflation for the everting balloon 18.

The everting balloon system 2 can seal the cervical canal, for example, as follows:
  a. The everting balloon 18 can be pressurized by an inflation device or air/liquid pump before placing the device adjacent to a cervix.
  b. The distal end of the everting balloon system 2 can be placed at the patient's cervix.
  c. The position of the everting balloon system 2 can be maintained throughout the procedure (e.g., the device can operate via one-handed operation).
  d. The inner catheter 8 and everting balloon membrane 24 can be distally advanced through the cervical canal.
  e. The transfer catheter 156 can advanced distally through and beyond the everting balloon 18 or inner catheter 8.
  f. The transfer catheter 156 can deliver reproductive material 166 into the uterine cavity 176 or use a syringe 74 to deposit the reproductive material 166 through the proximal connector 206
  g. The inner catheter 8 and everting balloon 18 can then be proximally retracted with respect to the target site 164.
  h. The outer catheter 4 and inner catheter 8 can then be detached or decoupled from the distal closure tip 180 and removed proximally from the distal closure tip 180.

For example, the inflated distal tip can be left in the cervix and the everting balloon 18 can remain pressurized.

i. Part or all of the everting balloon system 2 can be left within the body for a pre-determined duration of time j. The pull string 184 can be pulled to remove the plug 182 and/or pressurization release check valves 188. The pull string 184 can be connected to the plug 182 to remove hydraulic pressure from the everting catheter system. The everting balloon 18 can deflate.

k. The pull string 184 can be attached to the everting balloon 18 and/or distal closure tip 180 and pulled to withdraw the deflated everting balloon 18 and/or distal closure tip 180 from the body.

The everting balloon system 2 can be inserted into and occlude the urethra, for example to treat urinary incontinence in the male or female. The everting balloon 18 can act as a urethral insert.

The everting balloon system 2 can create a seal in a urethral channel or passage. Once positioned into or at the urethral opening, the user can press the surface of the outer catheter distal tip 78 or everting balloon base against the urethral opening. The user can then activates the pressurization source and extrudes the everting balloon 18. The everting balloon system 2 can self-propel along the urethral channel. The balloon material occupies the inner lumen 8 of the urethra as it everts and thereby creates a sealing element. The everting balloon membrane 2 can be filled with saline, air, or a combination of both.

The everting balloon 18 can lock into place within the urethra. The everting balloon 18 can deliver radial forces to the inner lumen 8 of the urethra.

The everting balloon system 2 can be compact and designed for self-insertion and removal by the patient. Bladder voiding can occur after removal of all or part of the system from the urethral passage or after a sealing mechanism in the system is inactivated or removed.

Figure 13A:
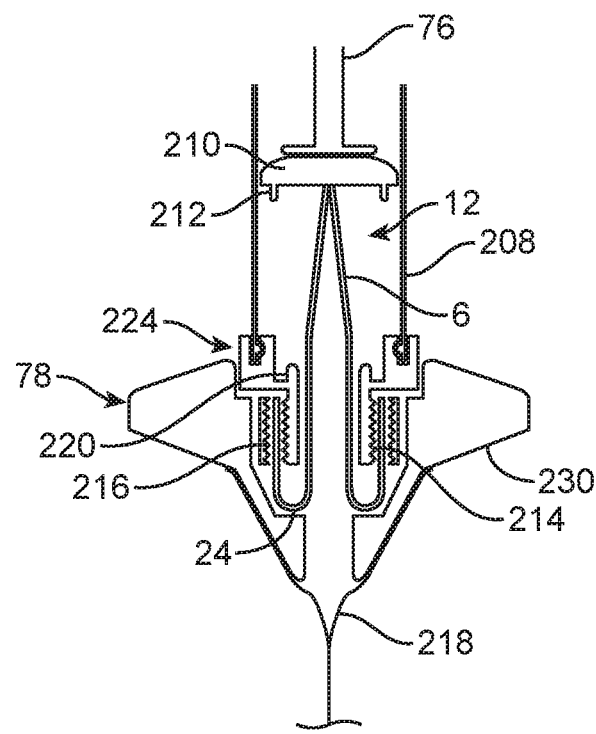
FIG. 13A is a cross-section view of a portion of a variation of the everting balloon system in a retracted configuration.

FIG. 13A illustrates that the everting balloon system 2 can have an outer catheter 4 that is a syringe housing 208. A plunger 76 within the syringe housing 208 can be distally detachably connected to a media volume cap 210. The plunger 76 can be proximally retracted, for example being ready for advancement. Part or all of the syringe housing 208, such as the portion within the everting balloon 18, can be filled with inflation media such as described herein. The syringe housing 208 and/or plunger 76 can be a reusable component of the everting balloon system 2 that is attached to the remainder of the everting balloon system 2 before deployment of the everting balloon 18 by the user.

Cap lock pegs 212, collars, grooves, or a luer fitting can extend distally from or proximally into the radially outer portions of the distal and/or radial sides of the media volume cap 210.

The radially inner terminal end of the everting balloon membrane 24 can be attached to the radially central portion of the cap lock. The cap lock can form a fluid-tight seal against the radial inside of the syringe housing 208.

The outer catheter distal tip 78 can have a distal tip membrane interface 214. The distal tip membrane interface 214 can have teeth or texturing (e.g., knurling, ridges, bumps) extending radially outwardly. The radially outer end of the balloon membrane 6 can attach to the distal tip membrane interface 214. The outer catheter distal tip 78 can have an everting balloon membrane collar 216. The everting membrane collar 216 can have teeth or texturing (e.g., knurling, ridges, bumps) extending radially inwardly. The radially outer end of the balloon membrane 6 can be squeezed between the everting membrane collar 216 and the distal tip membrane interface 214 to attach to the outer catheter distal tip 78.

The outer catheter distal tip 78 can have a flange radially extending from the remainder of the outer catheter distal tip 78. The user can identify the urethral opening. The outer catheter distal tip 78 can be positioned at the urethra opening and then translated and inserted into the urethra 218. As the outer catheter distal tip 78 is translated into the urethra 218, the urethra 218 can abut the flange, for example to stop translation of the outer catheter distal tip 78 with respect to the urethra 218. The flange can be outside of the urethra 218 in the male and outside the urethra 218 in the vagina in the female. The outer catheter distal tip 78 can be made from a low durometer, soft and conformable biocompatible material such as silicone.

The distal end of the syringe housing 208 can detachably connect to the proximal end of the outer catheter distal tip 78 at a fluid-tight tip connector. For example, the distal end of the syringe housing 208 can detachably connect to the proximal end of the outer catheter distal tip 78 at a circumferential snap connector or luer connector.

Cap lock ports 220, collars, grooves, or a luer fitting can extend distally from or proximally into the radially outer portions of the distal and/or radial sides of the media volume cap 210.

The outer catheter distal tip 78 can act as the distal closure tip 180.

The syringe housing 208 can be used as a handle to manipulate the position and orientation of the system.

Figure 13B:
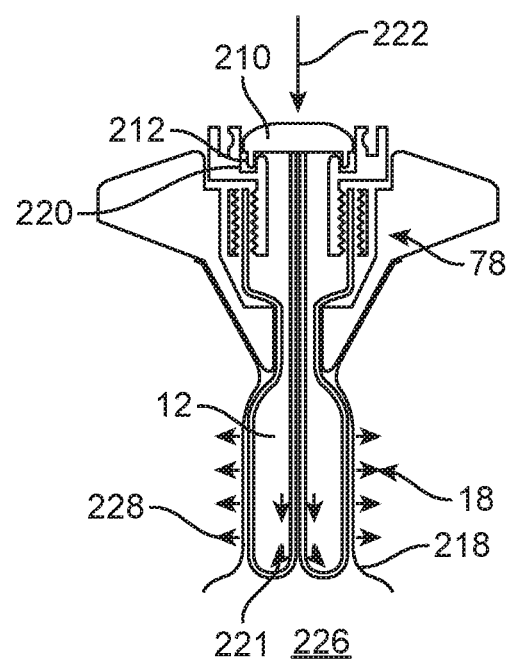
FIG. 13B is a cross-section view of a portion of a variation of the everting balloon system in an extended or everted configuration.

FIG. 13B illustrates that the plunger 76 can be depressed or translated, as shown by arrow 222, toward the outer catheter distal tip 78, for example translating the media volume cap 210 to press into the proximal end of the outer catheter distal tip 78.

The radially inner end of the balloon membrane 6 and the inflation media in the media volume 12 can be pressed distally, for example, causing the everting balloon 18 to propel, unroll and evert, as shown by arrows 221, into the urethra 218. The cap lock peg 212 can engage and attach the cap lock port 220. The cap lock peg 212 attached to the cap lock port 220 can form a fluid-tight seal. When the cap lock peg 212 attached to the cap lock port 220, a palpable disengagement of the syringe housing 208 can be felt by the user. The plunger 76 and syringe housing 208 can have thumb and finger rings, for example to separately control the plunger 76 and the syringe housing 208 with a single hand.

The syringe housing 208 can be disengaged and detached from the inflation check valve and/or outer catheter distal tip 78 at the tip connector 224 and removed. The syringe housing 208 can disengage from the outer catheter distal tip 78 concurrently or subsequently to the cap lock peg 212 attaching to the cap lock port 220.

The proximal end of the outer catheter distal tip 78 and/or the distal end of the syringe 74 can have a one-way inflation check valve, for example preventing or minimizing backflow of media 155 into the syringe 74. The everting balloon 18 can distend the urethra 218, as shown by arrows 228, and create a fluid-tight seal against the wall of the urethra 218. The everting balloon 18 can automatically traverse the urethra 218, for example, without delivering a shear force to the urethra wall. The everted balloon 18 can extend to the proximal terminal end of the urethra 218, into the bladder 226, or stop short of the proximal terminal end of the urethra 218.

Distal force can be delivered to the syringe housing 208, plunger 76, or outer catheter distal tip 78, for example to prevent dislodgement of the everting balloon 18 during eversion, such as at the beginning of eversion before the everting balloon 18 fixes to the urethra 218.

The everting balloon 18 can be pressurized and can plug and seal the passageway of the urethra 218.

The everting balloon 18 can seal throughout the urethral passageway by creating radial pressure throughout the urethra 218. Since the mechanism of action of the everting balloon 18 is independent of urethral length, a sizing procedure is not needed. Avoiding multiple sizes simplifies physician fitting and does not require greater inventory.

The everting balloon 18 can be soft and conformably anchored, for example, since the everting balloon 18 fills space and thus exerted pressure evenly along the length of the everting balloon 18 in the urethra 218. As the patient moves, bends, coughs, or provides pressure on the pelvic floor, the everting balloon 18 can conform to the shape of the urethra 218, maintaining a seal until removed or deflated, for example by the patient.

The system can include an everting balloon 18 that everts and expands immediately upon pressurization. This can be accomplished by having the most distal portion of the outer catheter distal tip 78 constructed with exposed everting balloon membrane 24. In use, the most distal portion of the outer catheter distal tip 78 can intubate the urethra 218 with the exposed portion of the everting balloon membrane 24 contacting the inner os of the urethra 218 for a distance of 1 to 5 mm. Thus at pressurization, the everting balloon membrane 24 can begin to lock into place and thereby reduce backing out. The remainder of the everting balloon 18 can be maintained within the case unit up until the pressurization process is initiated. In this fashion, the invasive portion of the everting balloon 18 that enters the urethra 218 can be protected from contact from the user hands and other areas that can contaminate the balloon 178.

The everting balloon membrane 24 can be housed completely within the distal outer catheter tip 78 with the most distal portion of the distal outer catheter tip 78 can be distensible and expand immediately upon pressurization of the everting balloon membrane 24. The distensible portion of the distal outer catheter tip 78 can radially expand and contact the inner wall of urethra 218 to provide locking forces.

A cylindrical open-ended tube can be used as an inserter to protect inadvertent contact of the everting balloon 18 from vaginal side walls, for example, to prevent contamination of the everting balloon 18 with vaginal flora or detritus during the insertion process.

Figure 13C:
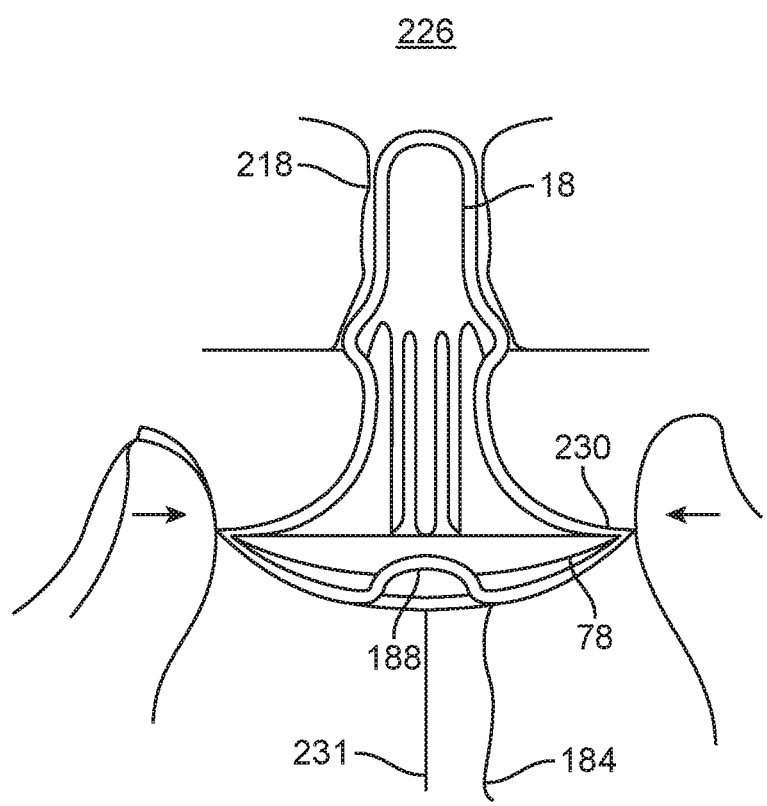
FIG. 13C illustrates a variation of a method for removing the everting balloon from a body lumen.

FIG. 13C illustrates that the everting balloon 18 can be deflated after insertion and deployment into the urethra 218. The everting balloon 18 can be removed from the urethra 218 and/or deflated, for example for bladder voiding (i.e., urinating). One or both of the flanges 230 can be pinched or compressed toward each other by the user to deform the outer catheter distal tip 78 and open the pressurization release check valve 188 in the outer catheter distal tip 78. The inflation media 231 can then exit the pressurization release check valve 188, deflating the everting balloon 18. The everting balloon 18 and outer catheter distal tip 78 can then be pulled out of the urethra 218 and removed from the patient.

The outer catheter distal tip 78 can have a pull string 184 attached to the proximal end of the remainder of the outer catheter distal tip 78. The pull string 184 can be pulled to remove the everting balloon 18 and outer catheter distal tip 78 (e.g., in the same fashion as the removal of a tampon).

Figure 14A:
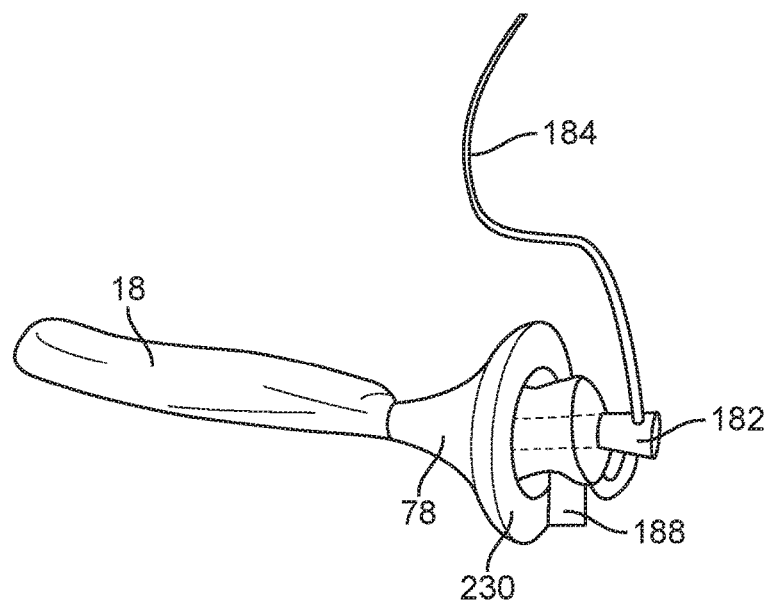
FIG. 14A illustrates a variation of a portion of the everting balloon system with the plug inserted in the outer catheter distal tip.
Figure 15A:
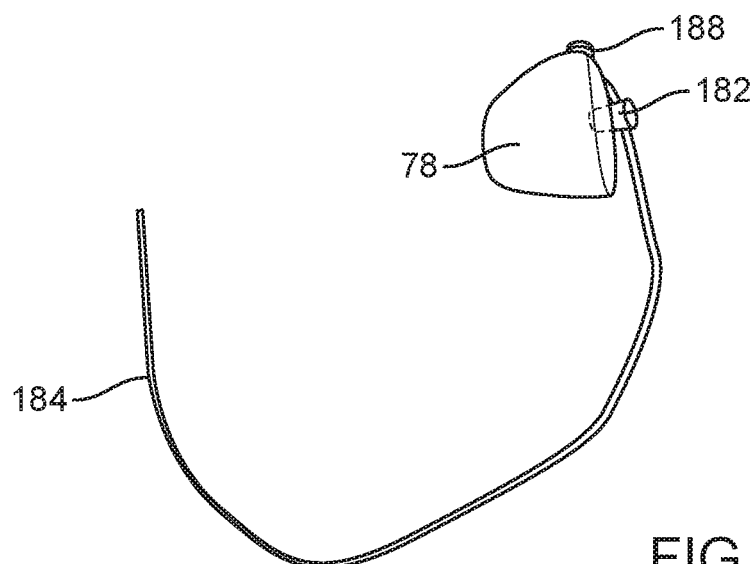
FIGS. 15A illustrates a variation of a portion of the everting balloon system with the plug not inserted in the outer catheter distal tip and the everting balloon in a retracted configuration.
Figure 15B:
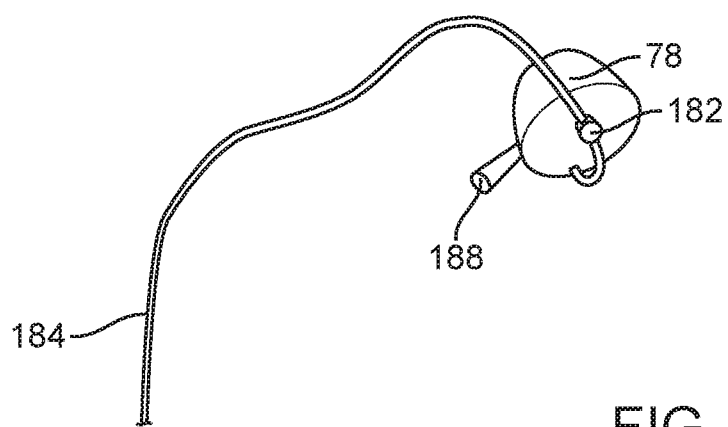
FIGS. 15B and 15C illustrate the variation of the portion of the everting balloon system of FIG. 15A with the plug inserted in the outer catheter distal tip and the everting balloon in a retracted configuration.

FIGS. 14A, 15A and 15B illustrate that the outer catheter distal tip 78 can have a pressurization release check valve 188 through which the media 155 can enter to pressurize and inflate the everting balloon 18. The pressurization release check valve 188 can be a one-way valve preventing or minimizing media 155 flow out of the everting balloon 18 to the surrounding environment. For example, the pressurization release check valve 188 can have a duck bill or micro valve. The plug 182 and external port of the respective pressurization release channel 186 can be located radially central on the proximal side of the outer catheter distal tip 78.

Figure 14B:
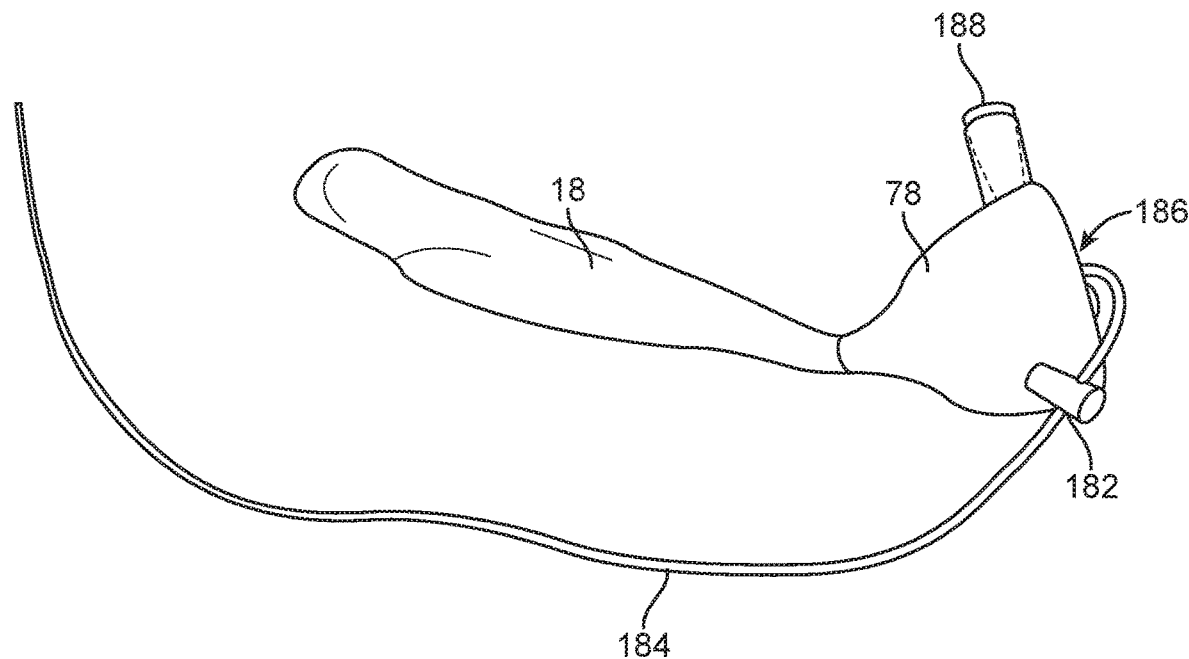
FIG. 14B illustrates the variation of the portion of the everting balloon system from FIG. 14A with the plug not inserted in the outer catheter distal tip.
Figure 15C:
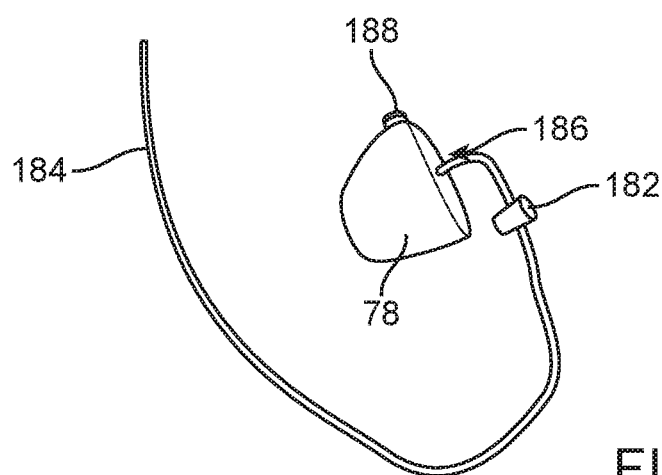

FIGS. 14B and 15C illustrate that the pull string 184 can be fixed to the body of the outer catheter distal port 80. The plug 182 can be attached to the pull string 184. For example, the pull string 184 can extend through the plug 182. For example, the plug 182 can be glued to, welded to, clipped to, or over-molded onto the pull string 184. The pull string 184 can be pulled to remove the plug 182 from the external port of the pressurization release channel 186, and the media 155 from the everting balloon 18 can then be released to the surrounding environment. The everting balloon 18 can then depressurize and deflate. The pull string 184 can be pulled, removing the outer catheter distal tip 78 and everting balloon from the urethra 218.

Once the positive lock mechanism is defeated by the pulled string 184, the everting balloon 18 is deflated and the entire device can be removed and disposed.

FIGS. 14A and 14B illustrate that the distal terminal end of the outer catheter distal tip 78 can have a distally protruding, pointed, acorn, nipple, or conical shape configuration.

FIGS. 15A through 15C illustrate that the distal terminal end of the outer catheter distal tip 78 can have a smooth, rounded, concave shape that can minimize intubation into the urethra 218.

Figure 16A:
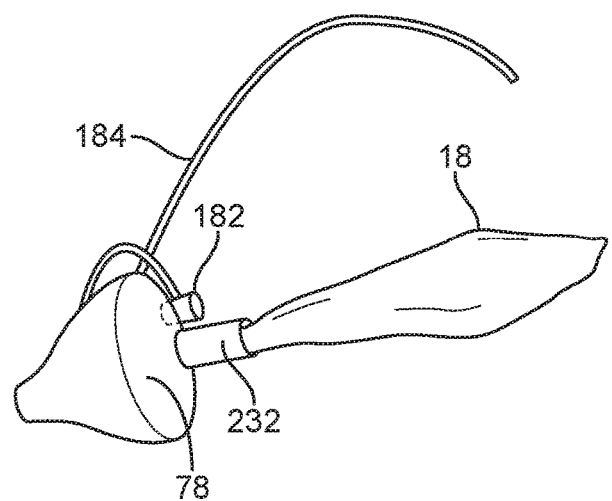
FIGS. 16A and 16B illustrate a variation of a portion of the everting balloon system with the everting balloon in everted and retracted configurations, respectively.
Figure 16B:
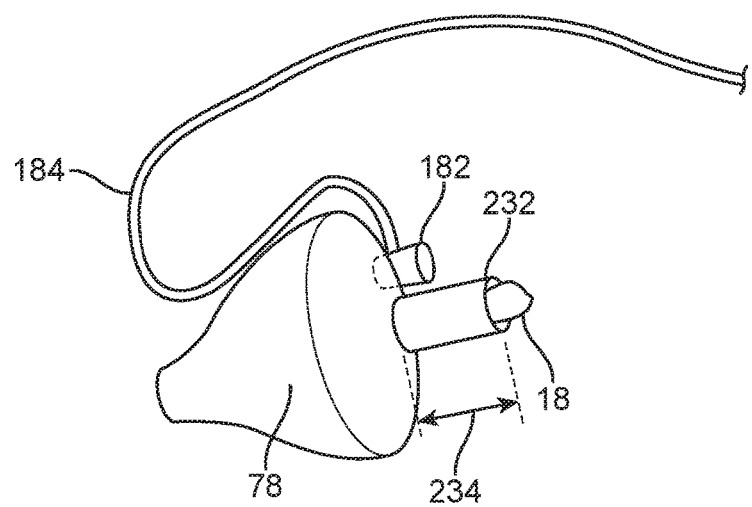

FIGS. 16A and 16B illustrate that the outer catheter distal tip 78 can have a tip distal extension 232. The tip distal extension 232 can extend distally from the remainder of the outer catheter distal tip 78. The tip distal extension 232 can have a tip distal extension length 234. The tip distal extension length 234 can be from about 1 mm to about 4 mm. The tip distal extension 232 can be cylindrical. The tip distal extension 232 can be inserted into the body lumen, such as the urethra 218, before the everting balloon 18 is everted.

Figure 17:
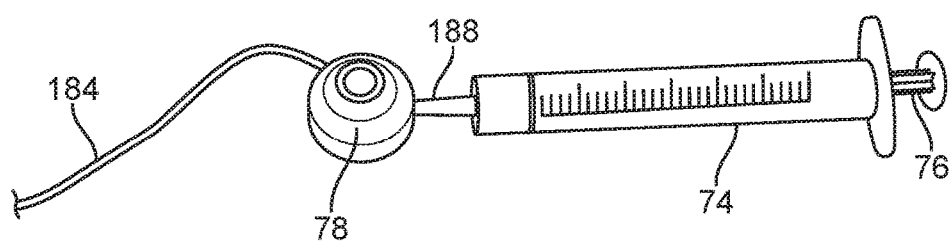
FIG. 17 illustrates a variation of a method for pressurizing the everting balloon.

FIG. 17 illustrates that the inflation device can be a syringe 74. The syringe 74 can be connected to the pressurization release check valve 188. The plunger 76 can be depressed into the syringe 74, delivering media 155 under pressure through the pressurization release check valve 188 and into the everting balloon 18, for example, to inflate, expand, advance, propel, and evert the everting balloon 18.

Figure 18A:
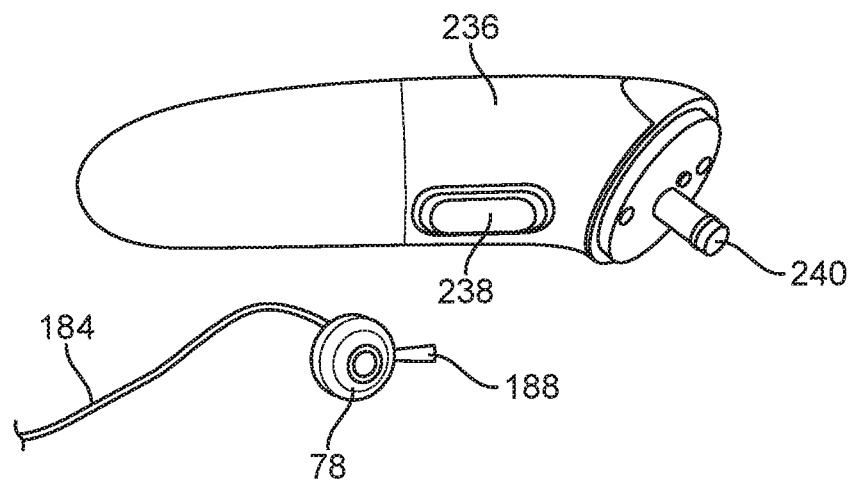
FIGS. 18A and 18B illustrate a variation of a method for pressurizing the everting balloon.
Figure 18B:
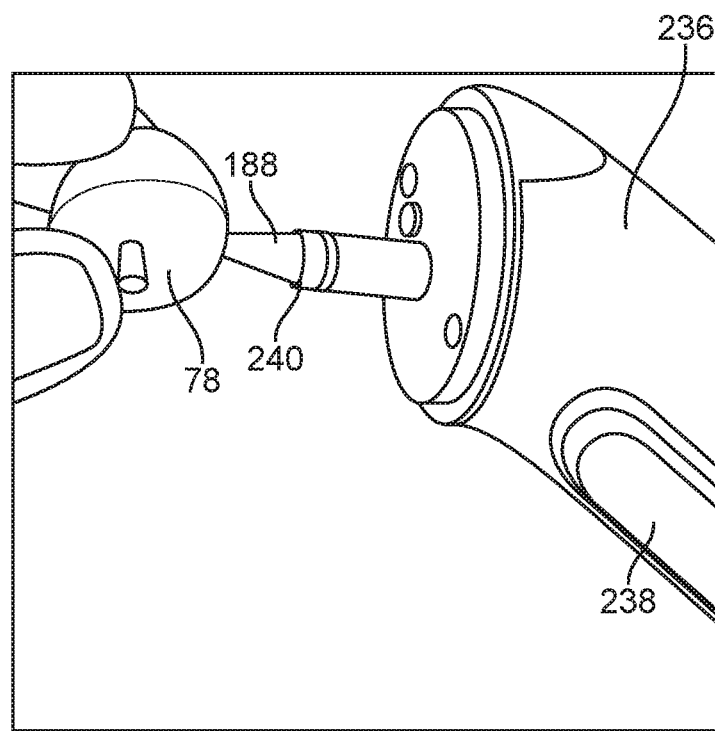

FIGS. 18A and 18B illustrate that the inflation device can be a small motorized air (or other gas or liquid) pump 236. The pump 236 can have a pump power switch 238 to control the pressure delivery from the pump 236. The pump power switch 238 can be a push button or toggle. The pump power switch 238 can control the flow rate and pressure of the media 155 delivery from the pump 236. The pump 236 can have a pump outlet 240 configured to deliver pressurized media 155. The pump outlet 240 can connect to the pressurization release check valve 188. The pump power switch 238 can be turned to an on position. The motorized air pump 236 can then deliver pressurized media 155 through the pressurization release check valve 188 and into the outer catheter distal tip 78. The pressurized media 155 can, for example, inflate, expand, advance, propel, and evert the everting balloon 18.

The pump 236 can deliver air or other media 155 directly into the everting balloon 18. The air pump 236 can be connected to the base of the everting balloon 18. The distal tip of the everting balloon 18 can be placed at the urethral opening.

The pump 236 can be configured to stall, a pressure relief valve, or other pressure check valve mechanism can open, or combinations thereof, if the pump outlet 240 pressure exceeds a maximum pressure limit of the everting balloon 18.

After pressurization of the everting balloon 18, the pump 236 can be disconnected from the pressurization release check valve 188, for example by the depression of a release button or can automatically be disengaged upon stalling the pump 236 or by the activation of the pressure relief valve within the air pump. The increase of pressure within the everting balloon 18 can automatically disconnect the air pump from the everting balloon 18 and/or pressurization release check valve 188.

The outer catheter distal tip 78 (i.e., the base of the everting balloon 18) can be small and made from a soft durometer material, with a shallow profile for comfortable wearing for the patient. The outer catheter distal tip 78 can have a rounded, smooth, domed, or disk-like shape. The outer catheter distal tip 78 can have a pillow-like feel. The outer catheter distal tip 78 can be manufactured with two molded halves with an internal, circumferential attachment ring.

The pressurization release check valve 188 can be engaged to the pump 236 with an internal locking ring that can be disengaged either through a manual actuator or automatically as described above.

The everting balloon system 2 can have a pressure indicator. The pressure indicator can indicate (e.g., via a light, buzzer, mechanical indicator such as a compliant dimple) if the desired pressure is not achieved, for example signifying a leak in the everting balloon system 2. The user can be alerted that the everting balloon system 2 is not patent and should not be relied upon for effectiveness (e.g., urinary control).

The pump 236 can be a reusable, small profile, battery operated, air pump. The pump 236 can allow for insertion and control of the everting balloon 18 and outer catheter distal tip 78 at the urethra 218, inflation of the everting balloon 18, and can be disengaged from the everting balloon 18 automatically or through a push button control or other actuator. As an example, the air pump 236 can have a check valve for pressure relief at or below about 380 mmHg (0.5 atm) or about 7 psi (0.5 atm), for example, for inflation and sealing during exercise, coughing, and other pelvic floor movements by the user.

The air pump 236 can be washed and replaced after a predetermined number of uses or applications before an internal battery is expended or replaced. The everting balloon 18 can be mounted onto the distal end of the air pump 236, for example on or around the pump outlet 240.

The air pump 236 can provide be operated with no manual manipulations by the user for inflation or locking air pressure. The air pump 236 can be quiet and water-tight, for example to prevent leaking into the pump 236 during cleaning.

The pump 236 can be connected to the everting balloon 18 or outer catheter distal tip 78 by a section of tubing, for example to provide strain relief or more degrees of freedom in terms of insertion angle of the everting balloon 18. The air pump 236 attached to the everting balloon 18 can be delivered to the target site 164 with one hand.

The inflation device can be or have a prefilled gas canister or ampule. The canister can be carbon dioxide ($CO_2$) or nitrous oxide capsules.

The everting balloon 18 can be pressurized with liquid (hydraulic) and/or gas (pneumatic) pressure. Liquid, such as water or saline, can be lubricous and incompressible. The liquid can deliver a higher traversing force for the everting balloon than a gas. Gas, such as carbon dioxide, nitrous oxide, nitrogen, or air, can be lighter than liquid.

The external surface of the everting balloon 18 and/or outer catheter distal tip 78, for example the areas interfacing the urethra 218, can be coated or covered by conformable protrusions, gel or jelly, an adhesive-like covering, for example to secure to the target body lumen wall and prevent leaks, or combinations thereof. The coating on the external surface of the everting balloon 18 can have anti-bacterial and/or anti-infection properties and/or agents to reduce the potential for infection. The coating can contain anesthetic and analgesic properties or agents (e.g. lidocaine) to reduce discomfort and/or other drugs, therapeutic agents, compounds, or combinations thereof. The external surface of the everting balloon 18 and/or outer catheter distal tip 78, for example the areas interfacing the urethra 218, can be conformable and soft, for example to fill the target body lumen.

The everting balloon 18 can be sterile before eversion. For example, all portions of the everting balloon 18 can be contained inside the base when the system is positioned adjacent to the opening of the urethra 218. The distal outer catheter tip 78 can be contained within an insertion tube during the insertion process.

Deployment of the everting balloon 18 can be atraumatic. For example, the everting balloon 18 can roll inside the body lumen (e.g., urethra) without any translational (i.e., shear) or frictional forces on the lumen wall.

The patient can keep and store additional everting balloon 18 and outer catheter distal tips 78 on their person.

As shown for example in FIGS. 13A through 18B, the outer catheter distal tip 78 does not need to attach to a catheter to be used. The outer catheter distal 78 tip can be used by attaching to a pressurized media 155 source (e.g., a catheter, syringe, pump, or combinations thereof), force delivery element (e.g., a plunger), having an on-board pressure source in the outer catheter distal tip 78, or combinations thereof. The outer catheter distal tip 78 is also referred to as the base.

After the everting balloon system 2 is pressurized and positioned in the cervix, the inner catheter 8 can be distally advanced toward the target body cavity by hand or with a one-handed control system, such as the system handle 30. The system handle 30 can allow the user to hold the entire catheter system and manipulate the pressurization, movement of components, and de-pressurization of the balloon membrane 6 with one hand. The user can then utilize the other hand for the manipulation of instruments, controlling ultrasound, handling visualization techniques, depositing materials within the through-lumen by use of another syringe or delivery device mechanism, or combinations thereof.

Any elements described herein as singular can be pluralized (i.e., anything described as "one" can be more than one). Any species element of a genus element can have the characteristics or elements of any other species element of that genus. "Dilation" and "dilatation" are used interchangeably herein. The media 155 delivered herein can be any of the fluids (e.g., liquid, gas, or combinations thereof) described herein. The patents and patent applications cited herein are all incorporated by reference herein in their entireties. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, and methods described herein can be used for medical (e.g., diagnostic, therapeutic or rehabilitative) or non-medical purposes.

We claim:

1. A method for delivering matter into the reproductive tract of a female comprising a cervical canal, the method comprising:
　retracting a first catheter having a lumen and a distal lumen port, wherein an everting balloon is attached to the first catheter;
　extending the first catheter, wherein extending the first catheter comprises extending at least a length of the everting balloon past the distal lumen port of the first catheter;
　sliding a second catheter located in the first catheter, wherein the sliding comprises pulling the second catheter distally through the cervical canal by everting the everting balloon;
　delivering an endoscope held by the second catheter into the reproductive tract of the female, and wherein the delivering comprises increasing the diameter of the cervix; and
　sealing the cervical channel with the everting balloon wherein the sealing comprises occluding the entire cervical channel after the delivering of the endoscope.

2. The method of claim 1, further comprising delivering a biopsy device.

3. The method of claim 1, further comprising transporting a reproductive material through the first catheter into the uterine cavity, and wherein sealing the cervical channel comprises occluding the cervical channel with the everting balloon after transporting of the reproductive material.

4. A method for delivering matter into the reproductive tract of a female comprising a cervical canal, the method comprising:
　retracting a first catheter having a lumen and a distal lumen port, wherein an everting balloon is attached to the first catheter;
　extending the first catheter, wherein extending the first catheter comprises extending at least a length of the everting balloon past the distal lumen port of the first catheter;
　sliding a second catheter located in the first catheter, wherein the sliding comprises pulling the econd catheter distally through the cervical canal by everting the everting balloon;
　delivering an endoscope held by the second catheter into the reproductive tract of the female, wherein the delivering comprises increasing the diameter of the cervix; and
　sealing the cervical channel with the everting balloon, wherein the sealing comprises occluding the entire cervical canal with the everting balloon after transporting a biopsy device to the uterine cavity.

5. The method of claim 4, further comprising delivering a brush.

6. The method of claim 4, further comprising fluidly sealing a distal lumen port of the second catheter with respect to the uterine cavity.

7. The method of claim 4, further comprising inflating the everting balloon distal to the distal lumen port.

8. A method for delivering matter into the reproductive tract of a female comprising a cervical canal, the method comprising:
　retracting a first catheter having a lumen and a distal lumen port, wherein an everting balloon is attached to the first catheter;
　extending the first catheter, wherein extending the first catheter comprises extending at least a length of the everting balloon past a distal lumen port of the first catheter;
　sliding a second catheter located in the first catheter, wherein the sliding comprises pulling the second catheter distally through the cervical canal by everting the everting balloon;
　delivering a biopsy device held by the second catheter into the reproductive tract of the female, wherein the delivering comprises increasing the diameter of the cervix; and
　sealing the cervical channel with the everting balloon, wherein the sealing comprises occluding the entire cervical channel after the delivering of the biopsy device.

9. The method of claim 8, further comprising delivering a brush.

10. The method of claim 8, further comprising fluidly sealing a distal lumen port of the second catheter with respect to the uterine cavity.

11. The method of claim 8, further comprising inflating the everting balloon distal to the distal lumen port.

12. A method for delivering matter into the reproductive tract of a female comprising a cervical canal, the method comprising:
　retracting a first catheter having a lumen and a distal lumen port, wherein an everting balloon is attached to the first catheter;
　extending the first catheter, wherein extending the first catheter comprises extending at least a length of the everting balloon past a distal lumen port of the first catheter;
　sliding a second catheter located in the first catheter, wherein the sliding comprises pulling the second catheter distally through the cervical canal by everting the everting balloon;
　transporting a reproductive material through the first catheter into the uterine cavity;
　delivering an endoscope held by the second catheter into the reproductive tract of the female, wherein the delivering comprises increasing the diameter of the cervix; and
　sealing the cervical channel with the everting balloon, wherein the sealing comprises occluding the entire cervical channel after the delivering of the endoscope and occluding the cervical channel with the everting balloon after the transporting of the reproductive material.

13. The method of claim 12, wherein at least a length of the everting balloon extends past the distal lumen port of the first catheter when the first catheter is in the extended configuration.

14. The method of claim 12, further comprising a fallopian tube occluding device, wherein the second catheter is configured to deliver the fallopian tube occluding device.

15. The method of claim 12, further comprising a handle configured to control the eversion of the everting balloon, wherein the handle is configured to control translation of the second catheter.

16. The method of claim 14, further comprising a fallopian tube occluding device, wherein the second catheter is configured to deliver the fallopian tube occluding device.

17. The method of claim 14, further comprising a handle configured to control the eversion of the everting balloon, wherein the handle is configured to control translation of the second catheter.

18. The method of claim 15, further comprising a handle configured to control the eversion of the everting balloon, wherein the handle is configured to control translation of the second catheter.

19. The method of claim 17, further comprising a handle configured to control the eversion of the everting balloon, wherein the handle is configured to control translation of the second catheter.

\* \* \* \* \*